(12) United States Patent
Kannt et al.

(10) Patent No.: US 11,352,405 B2
(45) Date of Patent: Jun. 7, 2022

(54) GLP-1/GLUCAGON RECEPTOR AGONISTS IN THE TREATMENT OF FATTY LIVER DISEASE AND STEATOHEPATITIS

(71) Applicant: SANOFI, Paris (FR)

(72) Inventors: Aimo Kannt, Frankfurt am Main (DE); Maximilian Bielohuby, Frankfurt am Main (DE); Ralf Elvert, Frankfurt am Main (DE); Michael Wagner, Frankfurt am Main (DE); Martin Bossart, Frankfurt am Main (DE); Torsten Haack, Frankfurt am Main (DE); Stephanie Keil, Frankfurt am Main (DE); Werner Seiz, Frankfurt am Main (DE)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 16/637,517

(22) PCT Filed: Aug. 8, 2018

(86) PCT No.: PCT/EP2018/071478
§ 371 (c)(1),
(2) Date: Feb. 7, 2020

(87) PCT Pub. No.: WO2019/030268
PCT Pub. Date: Feb. 14, 2019

(65) Prior Publication Data
US 2020/0216510 A1 Jul. 9, 2020

(30) Foreign Application Priority Data

Aug. 9, 2017 (EP) ..................... 17306059

(51) Int. Cl.
| | |
|---|---|
| *A61K 38/00* | (2006.01) |
| *A61K 38/22* | (2006.01) |
| *A61K 38/26* | (2006.01) |
| *A61K 45/06* | (2006.01) |
| *A61P 1/16* | (2006.01) |
| *A61P 3/10* | (2006.01) |
| *C07K 14/605* | (2006.01) |

(52) U.S. Cl.
CPC .............. *C07K 14/605* (2013.01); *A61P 1/16* (2018.01); *A61P 3/10* (2018.01); *A61K 38/00* (2013.01); *A61K 45/06* (2013.01)

(58) Field of Classification Search
None
See application file for complete search history.

(56) References Cited

U.S. PATENT DOCUMENTS

| | | | |
|---|---|---|---|
| 2014/0100156 A1* | 4/2014 | Haack | A61P 9/00 514/1.9 |
| 2017/0114115 A1 | 4/2017 | Alsina-Fernandez et al. | |

FOREIGN PATENT DOCUMENTS

| | | |
|---|---|---|
| WO | WO 2014/056872 A1 | 4/2014 |
| WO | WO 2014/096145 A1 | 6/2014 |
| WO | WO 2016/198624 A1 | 12/2016 |
| WO | WO 2018/100174 A1 | 6/2018 |

OTHER PUBLICATIONS

Nonalcoholic steatohepatitis (NASH), Merck Manual, accessed Jul. 29, 2016 at URL merckmanual.com, pp. 1-3 (Year: 2016).*
Schaffler et al., "Mechanisms of Disease: adipocytokines and visceral adipose tissue—emerging role in nonalcoholic fatty liver disease" Nat. Rev. Gastroenterol. Hepat. 2:273-280 (2005) (Year: 2005).*
Chalasani et al., "The diagnosis and management of non-alcoholic fatty liver disease: practice Guideline by the American Association for the Study of Liver Diseases, American College of Gastroenterology, and the American Gastroenterological Association," Chalasani et al., Hepatol. 55:2005-2023 (2012)) (Year: 2012).*
Gastaldelli et al., "Time for Glucagon like peptide-1 receptor agonists treatment for patients with NAFLD?," J. Hepatol. 64:262-264 (Feb. 2016; electronically published Nov. 28, 2015) (Year: 2015).*
Medline Plus, obesity, available at http://www.nlm.nih.gov/medlineplus/obesity.html—(referenced Aug. 22, 2013) (Year: 2013).*
United Healthcare, diabetes, http://www.uhc.com/source4women/health_topics/diabetes/relatedinformation/d0f0417b073bf110VgnVCM1000002f10b10a_.htm—referenced Aug. 22, 2013 (Year: 2013).*
St. John Providence Health Center; Preventing Obesity; http://www.stjohnprovidence.org/HealthInfoLib/swarticle.aspx?type=85&id=P07863 (referenced Aug. 22, 2013) (Year: 2013).*
Church et al., "Association of Cardiorespiratory Fitness, Body Mass Index, and Waist Circumference to Nonalcoholic Fatty Liver Disease," Gastroenterology 130:2023-2030 (2006) (Year: 2006).*
Amarapurkar et al., "How common is non-alcoholic fatty liver disease in the Asia-Pacific region and are there local differences?", J Gastroenterol Hepatol. 2007,vol. 22, pp. 788-793.
Armstrong et al., "Liraglutide efficacy and action in non-alcoholic steatohepatitis (LEAN): study protocol for a phase II multicentre, double-blinded, randomised, contolled trial", BMJ Open 2013, vol. 3, e003995.
Armstrong et al., "Liraglutide safety and efficacy in patients with non-alcoholic steatohepatitis (LEAN): a multicentre, double-blind, randomised, placebo-controlled phase 2 study", Lancet 2016, vol. 387, pp. 679-690.

(Continued)

*Primary Examiner* — Julie Ha
*Assistant Examiner* — Kristina M Hellman
(74) *Attorney, Agent, or Firm* — Lathrop GPM LLP; James H. Velema, Esq.

(57) ABSTRACT

The present invention relates to the medical use of specific GLP-1/glucagon receptor agonists in the prevention and/or treatment of metabolic liver disease, particularly non-alcoholic fatty liver disease (NAFLD), more particularly non-alcoholic fatty liver (NAFL), non-alcoholic steatohepatitis (NASH) and/or NAFLD-associated liver fibrosis.

Figure 1A:
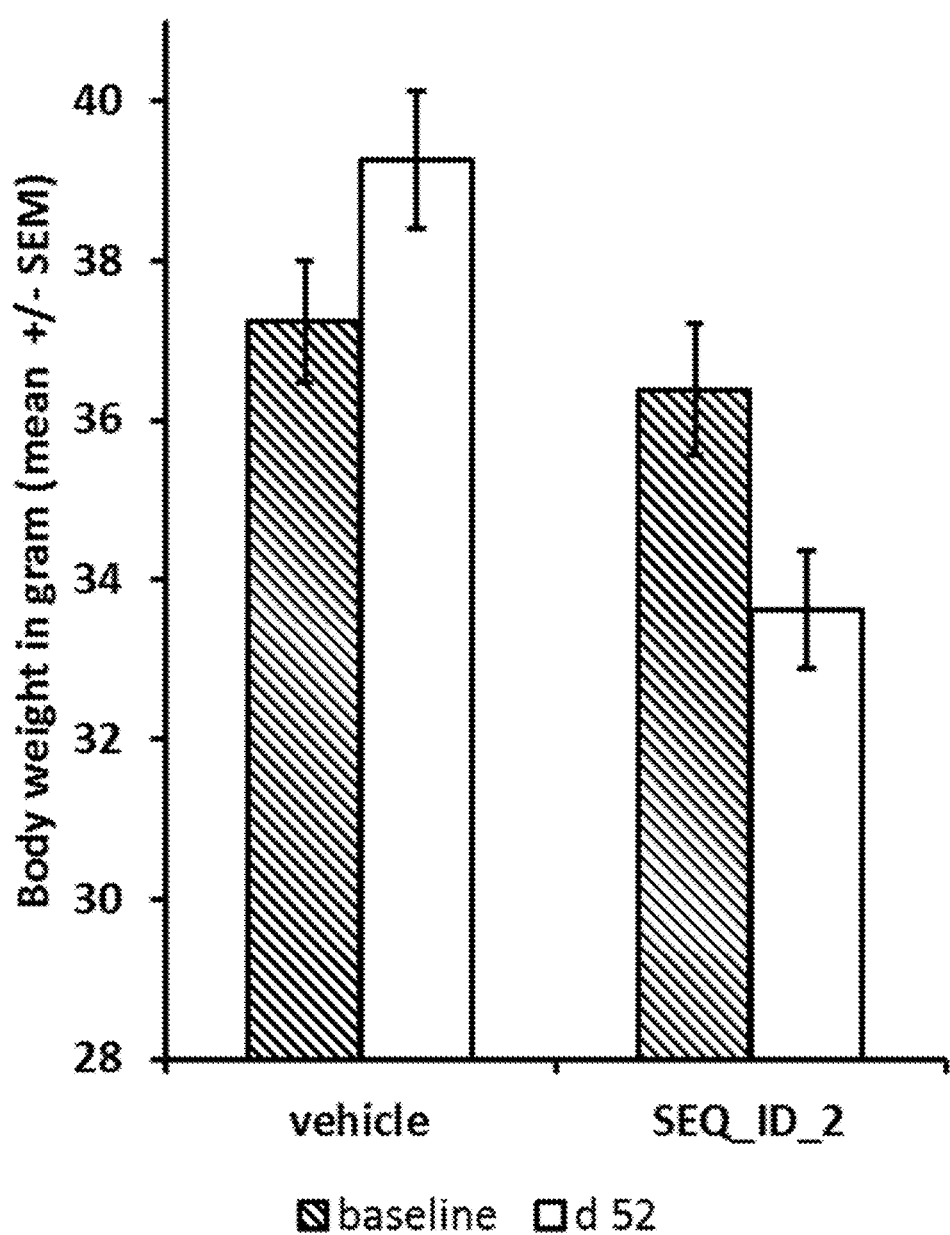

17 Claims, 16 Drawing Sheets
Specification includes a Sequence Listing.

(56) References Cited

OTHER PUBLICATIONS

Bataller et al., "Liver fibrosis", J Clin Invest. 2005, vol. 115, pp. 209-218.
Bedossa et al., "Histopathological Algorithm and Scoring System for Evaluation of Liver Lesions in Morbidly Obese Patients", Hepatology 2012, vol. 56, pp. 1751-1759.
Browning et al., "Prevalence of Hepatic Steatosis in an Urban Population in the United States: Impact of Ethnicity", Hepatology. 2004, vol. 40, pp. 1387-1395.
Bruix et al., "Management of Hepatocellular Carcinoma: An Update", Hepatology. 2011, vol. 53(3), pp. 1020-1022.
Buse et al., "Liraglutide once a day versus exenatide twice a day for type 2 diabetes: a 26-week randomised, parallel-group, multinational, open-label trial (LEAD-6)", Lancet 2009, vol. 374, pp. 39-47.
Calzadilla et al., "The Natural Course of Non-Alcoholic Fatty Liver Disease", Int J Mol Sci. 2016, vol. 17(5), pp. 774-785.
Clapper et al., "Diet-induced mouse model of fatty liver disease and nonalcoholic steatohepatitis reflecting clinical disease progression and methods of assessment", Am J Physiol Gastrointest Liver Physiol 2013, vol. 305, pp. G483-G495.
Drucker et al., "Liraglutide", Nature Drug Disc. Rev. 2010, vol. 9, pp. 267-268.
Dulai et al., "Increased Risk of Mortality by Fibrosis Stage in Nonalcoholic Fatty Liver Disease: Systematic Review and Meta-Analysis", Hepatology 2017, vol. 65, pp. 1557-1565.
Hagström et al., "Fibrosis stage but not NASH predicts mortality and time to development of severe liver disease in biopsy-proven NAFLD", Journal of Hepatology 2017, vol. 67, pp. 1265-1273.
International Preliminary Report on Patentability (Chapter II) in related PCT Applicaiton No. PCT/EP2018/071478 dated Aug. 30, 2019 (13 pages).
International Search Report and Written Opinion in related PCT Applicaiton No. PCT/EP2018/071478 dated Nov. 7, 2018 (14 pages).
Kleiner et al., "Design and Validation of a Histological Scoring System for Nonalcoholic Fatty Liver Disease", Hepatology 2005, vol. 41, pp. 1313-1321.
Kleiner et al., "Liver Histology and Clinical Trials for Nonalcoholic Steatohepatitis-Perspectives From 2 Pathologists", Gastroenterology 2015, vol. 149, pp. 1305-1308.
Kristiansen et al., "Obese diet-induced mouse models of nonalcoholic steatohepatitis-tracking disease by liver biopsy", World Journal of Hepatology 2016, vol. 8, pp. 673-684.
Lazo et al., "Prevalence of Nonalcoholic Fatty Liver Disease in the United States: The Third National Health and Nutrition Examination Survey, 1988-1994", Am J Epidemiol. 2013, vol. 178(1), pp. 38-45.
Ratziu et al., Elafibranor, an Agonist of the Peroxisome Proliferator—Activated Receptor—$\alpha$ and -$\delta$, Induces Resolution of Nonalcoholic Steatohepatitis Without Fibrosis Worsening Gastroenterology 2016, vol. 150, pp. 1147-1159.
Valdecantos et al., "A novel glucagon-like peptide 1/glucagon receptor dual agonist improves steatohepatitis and liver regeneration in mice", Hepatology, vol. 65, No. 3, Mar. 1, 2017 doi: 10.1002/hep.28962.
Vernon et al., "Systematic review: the epidemiology and natural history of non-alcoholic fatty liver disease and non-alcoholic steatohepatitis in adults", Alimwent Pharmacol Ther. 2011, vol. 34(3), pp. 274-285.
Williams et al., "Clinical Advances in Liver, Pancreas, and Biliary Tract", Gastroenterology, 2011, vol. 140(1), pp. 124-131.
Younossi et al., "Global Epidemiology of Nonalcohollic Fatty Liver Disease—Meta-Analytic Assessment of Prevalence, Incidence, and Outcomes", Hepatology 2016, vol. 64, pp. 73-84.

* cited by examiner

GLP-1/GLUCAGON RECEPTOR AGONISTS IN THE TREATMENT OF FATTY LIVER DISEASE AND STEATOHEPATITIS

RELATED APPLICATIONS

This application is a 35 U.S.C. § 371 filing of International Patent Application No. PCT/EP2018/071478, filed Aug. 8, 2018, which claims priority to European Patent Application No. 17306059.1, filed Aug. 9, 2017, the entire disclosures of which are hereby incorporated herein by reference.

FIELD OF THE INVENTION

The present invention relates to the medical use of specific GLP-1/glucagon receptor agonists in the prevention and/or treatment of metabolic liver disease, particularly non-alcoholic fatty liver disease (NAFLD), more particularly non-alcoholic fatty liver (NAFL), non-alcoholic steatohepatitis (NASH) and/or NAFLD-associated liver fibrosis.

BACKGROUND OF THE INVENTION

Fatty liver disease is a chronic condition characterized by excessive hepatic triglyceride deposition. It can be due to multiple causes, the major two forms being related to immoderate alcohol consumption or metabolic dysregulation in the absence of excessive alcohol intake. The latter has been termed non-alcoholic fatty liver disease (NAFLD). It is commonly linked to the metabolic syndrome and its individual components (obesity, type 2 diabetes mellitus, dyslipidemia and hypertension). The spectrum of NAFLD ranges from isolated hepatic steatosis also referred to as non-alcoholic fatty liver (NAFL) through non-alcoholic steatohepatitis (NASH) characterized by hepatic triglyceride accumulation, hepatocellular injury and lobular inflammation, to liver fibrosis. Of note, fibrosis can be present to various degrees in patients with NASH. The presence of NASH with fibrosis is a strong risk factor for development of cirrhosis and potentially hepatocellular carcinoma (Hagström et al., Journal of Hepatology 2017, vol. 67, pp. 1265-1273).

NAFLD is a common condition; global prevalence has been estimated to be as high as 25% (Younossi et al, Hepatology 2016, vol. 64, pp. 73-84). Transition from NAFL as a relatively benign condition to NASH and especially progression of fibrosis have been linked to an increase in risk of overall mortality (see, e.g., Dulai et al, Hepatology 2017, vol. 65, pp. 1557-1565).

Liraglutide is a marketed chemically modified analogue of glucagon-like peptide-1 (GLP-1) in which, among other modifications, a fatty acid is linked to a lysine in position 20 leading to a prolonged duration of action (Drucker et al., Nature Drug Disc. Rev. 2010, vol. 9, pp. 267-268; Buse et al., Lancet 2009, vol. 374, pp. 39-47).

The amino acid sequence of Liraglutide is shown as SEQ ID NO.: 4:

```
                                        (SEQ ID NO.: 4)
H-A-E-G-T-F-T-S-D-V-S-S-Y-L-E-G-Q-A-A-K((S)-4-

Carboxy-4-hexadecanoyl-amino-butyryl-)-E-F-I-A-

W-L-V-R-G-R-G-OH
```

Liraglutide acts as a GLP-1 receptor (GLP1R) agonist. Such GLP1R agonists have been demonstrated to lower blood glucose and reduce body weight. Moreover, treatment of obese patients with biopsy proven NASH with the GLP1R agonist liraglutide led to resolution of NASH in 39% of the patients, compared to 9% under placebo (Armstrong et al., BMJ Open 2013, vol. 3, e003995; Armstrong et al, Lancet 2016, vol. 387, pp. 679-690).

A pegylated synthetic analogue of oxyntomodulin, a dual agonist of GLP-1 and glucagon receptors, although with reduced affinity compared to the single agonists GLP-1 and glucagon, has been tested in a rodent model of NASH (Valdecantos et al., Hepatology 2017, vol. 65, pp. 950-968). The analogue, termed G49 and having a length of 29 amino acids, was analyzed in microarrays and liver regeneration after partial hepatectomy (PH).

WO 2014/056872 A1 and WO 2018/100174 A1, which are incorporated by reference herein, disclose exendin-4 derivatives which activate the GLP-1 and the glucagon receptor. In these exendin-4 derivatives, among other substitutions, methionine at position 14 is replaced by an amino acid carrying an $NH_2$ group in the side chain, which is further substituted with a non-polar residue (e.g. a fatty acid optionally combined with a linker).

No pharmacologic treatment of a condition pertaining to the spectrum of NAFLD has been approved by the medical authorities so far. Thus, a high need exists to identify new, safe, and effective drugs that can stop or reverse the time course towards advanced fibrosis or cirrhosis. A potentially useful medical intervention has to take into account the reversibility of the disease, the feasibility to identify respective patients and the intended treatment benefit, the duration of intervention needed to show results and safety profile of the medication.

BRIEF SUMMARY OF THE INVENTION

Provided herein is the medical use of specific dual GLP-1/glucagon receptor agonists in the prevention and/or treatment of metabolic liver disease, like non-alcoholic fatty liver disease (NAFLD), particularly non-alcoholic fatty liver (NAFL), non-alcoholic steatohepatitis (NASH) and/or NAFLD-associated liver fibrosis.

It was surprisingly found that peptidic compounds of formula A or salts or solvates thereof, which are derived from exendin-4 and (unlike exendin-4) potently activate both the GLP-1 and the glucagon receptor (e.g. WO2014/056872 A1), can be effectively used in the treatment of specific liver diseases like NAFLD, particularly NASH. All compounds of formula A are structurally closely related, having a length of 39 amino acids, an amidated C-terminus, and sharing an overall identity of 33 amino acids including a lysine at position X14 with a lipophilic modification.

Accordingly, the present invention is directed to a compound or salt or solvate thereof having the general formula A

```
His-(D-Ser)-Gln-Gly-Thr-Phe-Thr-Ser-Asp-Leu-Ser-

Lys-Gln-X14-X15-X16-X17-X18-Ala-X20-Asp-Phe-Ile-

Glu-Trp-Leu-Lys-X28-Gly-Gly-Pro-Ser-Ser-Gly-Ala-

Pro-Pro-Pro-Ser-NH₂
``` wherein

X14 is Lys, wherein the —NH$_2$ side chain group is functionalized by one of the groups selected from (S)-4-Carboxy-4-hexadecanoylamino-butyryl-(γE-Palm) and (S)-4-Carboxy-4-octadecanoylamino-butyryl-(γE-Stea);

X15 is Asp or Glu;
X16 is Ser or Glu;
X17 is Lys, Arg, or Gln;
X18 is Ala, Arg or Leu;
X20 is Gln or Lys; and
X28 is Ala or Asn;

for use in a method of preventing and/or treating metabolic liver disease.

In certain embodiments, the compound or salt or solvate thereof is a compound of formula A, wherein X14 is Lys, wherein the —NH$_2$ side chain group is functionalized by one of the groups selected from (S)-4-Carboxy-4-hexadecanoylamino-butyryl-(γE-Palm) and (S)-4-Carboxy-4-octadecanoylamino-butyryl-(γE-Stea);

X15 is Asp or Glu;
X16 is Ser or Glu;
X17 is Lys or Gln;
X18 is Ala or Leu;
X20 is Gln or Lys; and
X28 is Ala.

In other embodiments, the compound or salt or solvate thereof is a compound of formula A, wherein X14 is Lys, wherein the —NH$_2$ side chain group is functionalized by (S)-4-Carboxy-4-hexadecanoylamino-butyryl-(γE-Palm);

X15 is Asp or Glu;
X16 is Ser;
X17 is Lys or Arg;
X18 is Ala or Arg;
X20 is Gln; and
X28 is Ala or Asn.

In certain preferred embodiments, the compound is any one of SEQ ID NO.: 1, SEQ ID NO.: 2, or SEQ ID NO.: 3, or a salt or solvate thereof.

In some embodiments, the compound of formula A has a high solubility at an acidic pH, particularly between 3.5 and 5.5, more particularly about 4.5, and/or a physiological pH, particularly about 7.4, and wherein said solubility at said acidic and/or physiological pH is at least 0.5 mg/ml.

The invention further relates to a pharmaceutical composition comprising a compound or salt or solvate thereof of formula A as an active agent, together with at least one pharmaceutically acceptable carrier, for use in a method of preventing and/or treating metabolic liver disease. The pharmaceutical composition may, according to some embodiments, be administered parenterally, particularly injected.

According to some embodiments, the pharmaceutical composition may be administered in combination with at least one further therapeutically active ingredient. The pharmaceutical composition and the further therapeutically active ingredient or ingredients may be administered separately, contemporaneously or sequentially. The pharmaceutical composition and the further therapeutically active ingredient or ingredients may be administered at different time points, different frequencies and via different routes.

Within the general indication metabolic liver disease (characterized by hepatic fat deposition), it is particularly intended to use the compound or salt or solvate thereof of formula A or the pharmaceutical composition comprising such a compound in a method of preventing and/or treating non-alcoholic fatty liver disease (NAFLD). In another embodiment, the disease state to be prevented and/or treated is non-alcoholic fatty liver (NAFL), non-alcoholic steatohepatitis (NASH) and/or NAFLD-associated liver fibrosis.

According to certain embodiments, the compound or salt or solvate thereof of formula A or the pharmaceutical composition comprising such a compound is for use in a method of preventing and/or treating non-alcoholic steatohepatitis (NASH), particularly NASH associated with fibrosis.

According to other embodiments, the compound or salt or solvate thereof of formula A or the pharmaceutical composition comprising such a compound is for use in the prevention and/or treatment of sequelae of non-alcoholic steatohepatitis (NASH), particularly NAFLD-related liver cirrhosis and/or NAFLD-related hepatocellular carcinoma.

According to certain embodiments, the compound or salt or solvate thereof of formula A or the pharmaceutical composition comprising such a compound is for use in a method of simultaneously preventing and/or simultaneously treating NASH and additional pathological conditions or risk factors, particularly obesity and/or type 2 diabetes mellitus.

The present invention further relates to a method of preventing or treating metabolic liver disease in a patient in need thereof, comprising administering to said patient a therapeutically effective amount of a compound or salt or solvate thereof having the general formula A

```
His-(D-Ser)-Gln-Gly-Thr-Phe-Thr-Ser-Asp-Leu-Ser-
Lys-Gln-X14-X15-X16-X17-X18-Ala-X20-Asp-Phe-Ile-
Glu-Trp-Leu-Lys-X28-Gly-Gly-Pro-Ser-Ser-Gly-Ala-
Pro-Pro-Pro-Ser-NH₂
``` wherein

X14 is Lys, wherein the —NH$_2$ side chain group is functionalized by one of the groups selected from (S)-4-Carboxy-4-hexadecanoylamino-butyryl-(γE-Palm) and (S)-4-Carboxy-4-octadecanoylamino-butyryl-(γE-Stea);

X15 is Asp or Glu;
X16 is Ser or Glu;
X17 is Lys, Arg, or Gln;
X18 is Ala, Arg or Leu;
X20 is Gln or Lys; and
X28 is Ala or Asn.

DETAILED DESCRIPTION OF THE INVENTION

As already mentioned, the present invention is concerned with providing a new medical use, namely the prevention and/or treatment of metabolic liver disease, particularly NAFLD, more particularly NASH, of dual GLP-1/glucagon receptor agonist compounds of formula A.

The compounds of general formula A (His-(D-Ser)-Gln-Gly-Thr-Phe-Thr-Ser-Asp-Leu-Ser-Lys-Gln-X14-X15-X16-X17-X18-Ala-X20-Asp-Phe-Ile-Glu-Trp-Leu-Lys-X28-Gly-Gly-Pro-Ser-Ser-Gly-Ala-Pro-Pro-Pro-Ser-NH$_2$) or respective salts or solvates thereof are peptides having a length of 39 amino acids and one lipophilic side chain modification at the ε-amino group of the lysine residue at position X14 (K14).

The amino acid sequences of the present invention are described using the conventional one letter and three letter codes for naturally occurring amino acids. The peptidic compounds of formula A according to the present invention comprise a linear backbone of amino carboxylic acids linked by peptide, i.e. carboxamide bonds. The amino carboxylic acids may be α-amino carboxylic acids, for example L-α-amino carboxylic acids, unless indicated otherwise.

All compounds of formula A show a sequence identity over 33 out of 39 amino acids, i.e. about 85%, and have an unmodified N-terminus as well as an amidated C-terminus. The side chain modification at the ε-NH$_2$ group of K14 is selected from two alternatives, namely (S)-4-Carboxy-4-hexadecanoylamino-butyryl-(γE-Palm) and (S)-4-Carboxy-4-octadecanoylamino-butyryl-(γE-Stea). The formulae of γE-Palm and γE-Stea are represented in Table 1 below:

TABLE 1

Structural formulae of lipophilic side chain modifications (R = attachment point to ε-NH$_2$ of X14)

| cpd. | Formula |
|---|---|
| γE-Palm | 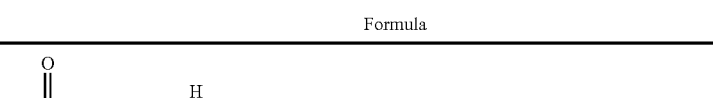 |
| γE-Stea | 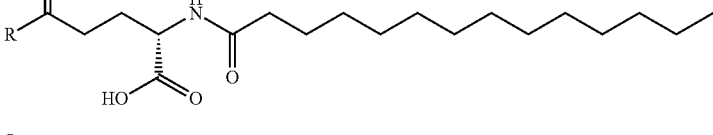 |

Only at six positions (X15, X16, X17, X18, X20 and X28), the amino acids are variable and are in each case selected from a maximum of three alternatives. Specifically, X15 may be aspartic acid (Asp) or glutamic acid (Glu), X16 may be serine (Ser) or glutamic acid (Glu), X17 may be lysine (Lys), arginine (Arg) or glutamine (Gln), X18 may be alanine (Ala), arginine (Arg) or leucine (Leu), X20 may be glutamine (Gln) or lysine (Lys) and X28 may be alanine (Ala) or asparagine (Asn).

In some embodiments of the compounds or salts or solvates of formula A, X14 is Lys, wherein the —NH$_2$ side chain group is functionalized by one of the groups selected from (S)-4-Carboxy-4-hexadecanoylamino-butyryl-(γE-Palm) and (5)-4-Carboxy-4-octadecanoylamino-butyryl-(γE-Stea);
 X15 is Asp or Glu;
 X16 is Ser or Glu;
 X17 is Lys or Gln;
 X18 is Ala or Leu;
 X20 is Gln or Lys; and
 X28 is Ala.

In other embodiments of the compounds or salts or solvates of formula A, X14 is Lys, wherein the —NH$_2$ side chain group is functionalized by (S)-4-Carboxy-4-hexadecanoylamino-butyryl-(γE-Palm);
 X15 is Asp or Glu;
 X16 is Ser;
 X17 is Lys or Arg;
 X18 is Ala or Arg;
 X20 is Gln; and
 X28 is Ala or Asn.

In certain preferred embodiments, the compound of formula A is any one of SEQ ID NO.: 1, 2 or 3, or a salt or solvate thereof.

In certain preferred embodiments, the isolated exendin-4 derivative of formula A or salt or solvate thereof has the amino acid sequence H-dS-Q-G-T-F-T-S-D-L-S-K-Q-K(γE-Palm)-E-S-K-A-A-Q-D-F-I-E-W-L-K-A-G-G-P-S-S-G-A-P-P-P-S-NH$_2$ (SEQ ID NO.: 1), with dS=D-serine. Compounds of SEQ ID NO.: 1 and their salts and solvates are particularly suitable for use in human medicine, because they show good binding to human GLP-1 and glucagon receptors.

According to other preferred embodiments, the compound of formula A or salt or solvate thereof has the amino acid sequence H-dS-Q-G-T-F-T-S-D-L-S-K-Q-K(γE-Palm)-D-S-R-R-A-Q-D-F-I-E-W-L-K-N-G-G-P-S-S-G-A-P-P-P-S-NH$_2$ (SEQ ID NO.: 2).

According to yet other preferred embodiments, the compound of formula A or salt or solvate thereof has the amino acid sequence H-dS-Q-G-T-F-T-S-D-L-S-K-Q-K(γE-Stea)-D-E-Q-L-A-K-D-F-I-E-W-L-K-A-G-G-P-S-S-G-A-P-P-P-S-NH$_2$ (SEQ ID NO.: 3).

The compounds of the invention are GLP-1 and glucagon receptor agonists as determined by the observation that they are capable of stimulating intracellular cAMP formation.

According to some embodiments, the compounds of the invention exhibit a relative activity of at least 0.1%, at least 0.2%, at least 0.3% or at least 0.4% compared to that of GLP-1(7-36) at the GLP-1 receptor. Furthermore, the compounds exhibit a relative activity of at least 0.1%, at least 0.2%, at least 0.3%, at least 0.4% or at least 0.5% compared to that of natural glucagon at the glucagon receptor.

The term "activity" as used herein particularly refers to the capability of a compound to activate the human GLP-1 receptor and the human glucagon receptor. In particular, the term "activity" as used herein refers to the capability of a compound to stimulate intracellular cAMP formation. The term "relative activity" as used herein is understood to refer to the capability of a compound to activate a receptor in a certain ratio as compared to another receptor agonist or as compared to another receptor. The activation of the receptors by the agonists (e.g. by measuring the cAMP level) is described in WO2014/056872 A1 or WO 2018/100174 A1.

According to one embodiment, the compounds of the invention have an EC$_{50}$ for the human GLP-1 receptor (hGLP-1 receptor) of 200 picomole per litre (pmol/l) or less, 50 pmol/l or less, or 5 pmol/l or less.

According to another embodiment, the compounds of the invention have an $EC_{50}$ for the human glucagon receptor (hGlucagon receptor) of 200 pmol/l or less, 50 pmol/l or less, or 10 pmol/l or less.

According to another embodiment, the compounds of the invention have an $EC_{50}$ for hGLP-1 receptor of 200 pmol/l or less, 50 pmol/l or less, or 5 pmol/l or less, and/or an $EC_{50}$ for hGlucagon receptor of 200 pmol/l or less, 50 pmol/l or less, or 10 pmol/l or less.

In still another embodiment, the $EC_{50}$ for both receptors i.e. for the hGLP-1 receptor and the hGlucagon receptor, is 100 pmol/l or less, 50 pmol/l or less, or 10 pmol/l or less. The $EC_{50}$ for hGLP-1 receptor and hGlucagon receptor may be determined as described in the Methods section of WO 2014/056872 A1.

The compound of formula A may be in the form of a salt, particularly a pharmaceutically acceptable salt, or a solvate, e.g. a hydrate. The term "pharmaceutically acceptable salt" means salts of the compounds of formula A which are safe and effective for use in mammals, particularly humans. Pharmaceutically acceptable salts may include, but are not limited to, acid addition salts and basic salts. Examples of acid addition salts include chloride, sulfate, hydrogen sulfate, (hydrogen) phosphate, acetate, citrate, tosylate or mesylate salts. Examples of basic salts include salts with inorganic cations, e.g. alkaline or alkaline earth metal salts such as sodium, potassium, magnesium or calcium salts and salts with organic cations such as amine salts. Further examples of pharmaceutically acceptable salts are described in Remington: The Science and Practice of Pharmacy, (20th ed.) ed. A. R. Gennaro, 2000, Lippencott Williams & Wilkins or in Handbook of Pharmaceutical Salts, Properties, Selection and Use, ed. P. H. Stahl, C. G. Wermuth, 2002, jointly published by Verlag Helvetica Chimica Acta, Zurich, Switzerland, and Wiley-VCH, Weinheim, Germany.

The term "solvate" means complexes of the compounds of the invention or salts thereof with solvent molecules, e.g. organic solvent molecules and/or water. In some embodiments, the solvate is a hydrate.

The compounds of formula A or salts or solvates thereof particularly may have a high solubility at an acidic pH and/or at a physiological pH. An acidic pH is typically below 7.0, particularly 5.5. More particularly, an acidic pH within the context of the invention is between 3.5 and 5.5, still more particularly about 4.5. The physiological pH in humans lies between 7.35 and 7.45, particular at about 7.4. In some embodiments, the compounds or salts or solvates of formula A show a high solubility at a physiological pH or at an acidic pH.

In certain embodiments, the compounds or salts or solvates of formula A show a high solubility at both a physiological pH and at an acidic pH. For example, compounds of formula A show a high solubility at both pH 7.4 and pH 4.5. "High solubility" as used herein refers particularly to a solubility of a given compound in aqueous solution at 25° C. of at least 0.5 mg/ml, at least 1.0 mg/ml, at least 5.0 mg/ml or more. In certain embodiments, the solubility of a compound of formula A or a salt or solvate thereof is >1000 mg/ml in aqueous solution at 25° C. at both an acidic pH of 4.5 and a physiological pH of 7.4.

A compound of formula A or a salt or solvate thereof may also be present as an active ingredient in a pharmaceutical composition.

The term "pharmaceutical composition" indicates a mixture containing ingredients that are compatible when mixed and which may be administered. A pharmaceutical composition may include one or more active ingredient(s). Additionally, the pharmaceutical composition may include carriers, buffers, acidifying agents, alkalizing agents, solvents, adjuvants, tonicity adjusters, emollients, expanders, preservatives, physical and chemical stabilizers e.g. surfactants, antioxidants and other components, whether these are considered active or inactive ingredients. Guidance for the skilled in preparing pharmaceutical compositions may be found, for example, in Remington: The Science and Practice of Pharmacy, (20th ed.) ed. A. R. Gennaro, 2000, Lippencott Williams & Wilkins and in R. C. Rowe et al. (ed.), Handbook of Pharmaceutical Excipients, PhP, May 2013 update.

The compounds of formula A of the present invention, or salts or solvates thereof, are particularly administered in conjunction with an acceptable pharmaceutical carrier, diluent, or excipient as part of a pharmaceutical composition. A "pharmaceutically acceptable carrier" is a carrier which is physiologically acceptable (e.g. physiologically acceptable pH) while retaining the therapeutic properties of the substance with which it is administered. Standard acceptable pharmaceutical carriers and their formulations are known to one skilled in the art and described, for example, in Remington: The Science and Practice of Pharmacy, (20th ed.) ed. A. R. Gennaro, 2000, Lippencott Williams & Wilkins and in R. C. Rowe et al (ed.), Handbook of Pharmaceutical excipients, PhP, May 2013 update. One exemplary pharmaceutically acceptable carrier is physiological saline solution.

In one embodiment carriers are selected from the group of buffers (e.g. citrate/citric acid, phosphate buffer such as sodium phosphate buffer), acidifying agents (e.g. hydrochloric acid), alkalizing agents (e.g. sodium hydroxide), preservatives (e.g. phenol, m-cresol), co-solvents (e.g. polyethylene glycol 400), tonicity adjusters (e.g. mannitol), stabilizers (e.g. surfactant, antioxidants, amino acids). The pharmaceutical composition may also comprise a combination of more than one of the above substances.

Concentrations used are in a range that is physiologically acceptable. In certain embodiments, administered doses may be between 20 and 500 μg per day. In certain embodiments, administered doses may be between 50 and 300 μg per day.

Acceptable pharmaceutical carriers or diluents include those used in formulations suitable for oral, rectal, nasal or parenteral (including subcutaneous, intramuscular, intravenous, intradermal, and transdermal) administration. The compounds of the present invention will typically be administered parenterally.

In the pharmaceutical composition, the compounds of formula A can be in monomeric or oligomeric form.

The term "therapeutically effective amount" of a compound refers to a nontoxic but sufficient amount of the compound to provide the desired effect. The amount of a compound of formula A necessary to achieve the desired biological effect depends on a number of factors, for example the specific compound chosen, the intended use, the mode of administration and the clinical condition of the patient. An appropriate "effective" amount in any individual case may be determined by one of ordinary skill in the art using routine experimentation. For example, the "therapeutically effective amount" of a compound of formula A is about 0.01 to 50 mg/dose, particularly 0.05 to 10 mg/dose. In certain embodiments, the therapeutically effective amount of a compound of formula A, particularly of SEQ ID NO.: 1, may be between 50 and 300 μg per day, or between 100 and 250 μg per day.

Pharmaceutical compositions of the invention are those suitable for parenteral (for example subcutaneous, intramuscular, intradermal or intravenous), oral, rectal, topical and peroral (for example sublingual) administration, although the most suitable mode of administration depends in each individual case on the nature and severity of the condition to be treated and on the nature of the compound of formula A used in each case. In certain preferred embodiments, the pharmaceutical composition comprising a compound of formula A is parenterally administered, particularly injected. In certain preferred embodiments, the injection is a subcutaneous injection.

Suitable pharmaceutical compositions may be in the form of separate units, for example capsules, tablets and powders in vials or ampoules, each of which contains a defined amount of the compound; as powders or granules; as solution or suspension in an aqueous or non-aqueous liquid; or as an oil-in-water or water-in-oil emulsion. It may be provided in single or multiple dose injectable form, for example in the form of a pen. The compositions may, as already mentioned, be prepared by any suitable pharmaceutical method which includes a step in which the active ingredient and the carrier (which may consist of one or more additional ingredients) are brought into contact.

The compound(s) of the present invention can be prepared for use in suitable pharmaceutical compositions. The suitable pharmaceutical compositions may be in the form of one or more administration units.

The compositions may be prepared by any suitable pharmaceutical method which includes a step in which the compound(s) of the present invention and the carrier (which may consist of one or more additional ingredients) are brought into contact.

The administration units may be for example capsules, tablets, dragées, granules, sachets, drops, solutions, suspensions, lyophylisates and powders, each of which contains a defined amount of the compound(s) of the present invention.

Each of the above-mentioned administration units of the compound(s) of the invention or pharmaceutical composition of the invention (administration units) may be provided in a package for easy transport and storage. The administration units are packaged in standard single or multi-dosage packaging, their form, material and shape depending on the type of units prepared. For example, tablets and other forms of solid administration units can be packaged in single units, and the single packaged units can be packaged in multi-pack containers. Liquid formulations can be packaged in single units, such as e.g. vials, cartridges, syringes/prefilled syringes, infusion bags, collapsible plastic bags, infusion bottles, blow-filled seal bottles or infusion tubings or in single or multiple dose injectable form, for example in the form of a pen device, pump or syringe and the single packaged units can be packaged in multi-pack containers. A single package may comprise only one or a plurality of administration units.

In certain embodiments administration units may be provided together with a device for application, for example together with a syringe, an injection pen or an autoinjector. Such devices may be provided separate from a pharmaceutical composition or prefilled with the pharmaceutical composition.

A "pen-type injection device", often briefly referred to as "injection pen", is typically an injection device having an elongated shape that resembles to a fountain pen for writing. Although such pens usually have a tubular cross-section, they could easily have a different cross-section such as triangular, rectangular or square or any variation around these geometries. Generally, pen-type injection devices comprise three primary elements: a cartridge section that includes a cartridge often contained within a housing or holder; a needle assembly connected to one end of the cartridge section; and a dosing section connected to the other end of the cartridge section. The cartridge, often also referred to as "ampoule", typically includes a reservoir that is filled with a medication, a movable rubber type bung or stopper located at one end of the cartridge reservoir, and a top having a pierceable rubber seal located at the other, often necked-down, end. A crimped annular metal band is typically used to hold the rubber seal in place. While the cartridge housing may be typically made of plastic, cartridge reservoirs have historically been made of glass.

The administration of the administration units (comprising a compound of formula A or a salt or solvate thereof) can e.g. take place once daily or twice daily. It is also possible to administer the administration units less frequently than once daily, e.g. once weekly. Any other administration frequency is also presently encompassed.

The administration of an administration unit can provide the peak plasma level of the compound of the invention within 0.02 hours to 72 hours after administration. The administration units included in one packaging can be substantially identical or they can be different, for instance can one packaging comprise administration units in solid and liquid form. One or more administration units can be administered on a first day, and one or more administration units can be administered on a second day following the first day, and the time interval between the administration of a unit and the administration of a subsequent unit can be 2 hours, or 4 hours, 6 hours or 8 hours, 12 hours or 24 hours, 36 hours or 48 hours.

In certain embodiments the pharmaceutical composition may be provided together with a device for application, for example together with a syringe, an injection pen or an autoinjector. Such devices may be provided separate from a pharmaceutical composition or prefilled with the pharmaceutical composition.

The compounds of formula A are suitable for therapeutic application without an additional therapeutically active ingredient. However, in some embodiments, the compounds or salts or solvates of formula A or a pharmaceutical composition comprising a compound or salt or solvate of formula A can also be administered in combination with at least one further therapeutically active ingredient. In the context of the present invention, the term "in combination with" means that the same patient is treated with a compound or salt or solvate of formula A or a pharmaceutical composition comprising a compound or salt or solvate of formula A and at least one further therapeutically active ingredient. The term does not mean that the different therapeutically active ingredients must be present in a single formulation. Rather, the compound of formula A or the pharmaceutical composition comprising the compound of formula A and the further therapeutically active ingredient or ingredients may be administered separately, contemporaneously or sequentially. The compound of formula A or the pharmaceutical composition comprising the compound of formula A and the further therapeutically active ingredient or ingredients may also be administered at different time points, at different frequencies and via different routes.

In certain embodiments, the compound of formula A or a pharmaceutical composition comprising a compound of formula A is administered in combination with exactly one further therapeutically active ingredient.

It is possible that the pharmaceutical composition comprises more than one compound of formula A or salts or solvates thereof. However, in certain embodiments, the pharmaceutical composition comprises exactly one compound of formula A, or a salt or solvate thereof.

In certain embodiments, the at least one further active ingredient is metformin, particularly metformin at a stable dose of 1500 mg/day or the maximal tolerated dose. Metformin is the international nonproprietary name of 1,1-dimethylbiguanide (CAS Number 657-24-9). In the present invention, the term "metformin" includes any pharmaceutically acceptable salt thereof.

Administration of the compound of formula A or pharmaceutical composition comprising a compound of formula A and the at least one further active ingredient, e.g. metformin, may be performed separately, contemporaneously, or sequentially.

A pharmaceutical composition comprising a compound of formula A and the at least one further therapeutically active ingredient or ingredients may be administered at different time points, different dosing frequencies and via different routes.

As mentioned above, the compounds of formula A or their salts or solvates are intended for a medical use, i.e. in the prevention and/or treatment of metabolic liver disease. In certain embodiments, the compounds are for use in a method of treating metabolic liver disease.

In one aspect, the invention relates to a compound or salt or solvate thereof having the general formula A as defined herein for use in a method of preventing and/or treating metabolic liver disease.

In another aspect, the invention relates to a pharmaceutical composition comprising a compound or salt or solvate thereof having the general formula A as defined herein for use in a method of preventing and/or treating metabolic liver disease. Within the pharmaceutical composition, the compound of formula A is an active agent, or, in some embodiments, the only active ingredient.

In yet another aspect, the invention relates to a method of preventing or treating metabolic liver disease in a patient in need thereof, comprising administering to said patient a therapeutically effective amount of a compound or salt or solvate thereof having the general formula A as defined herein.

In yet another aspect, the invention relates to a method of preventing or treating metabolic liver disease in a patient in need thereof, comprising administering to said patient a pharmaceutical composition comprising a therapeutically effective amount of a compound or salt or solvate thereof having the general formula A as defined herein.

As used herein, the term "metabolic liver disease" refers to alcohol-induced liver disease (also referred to as alcoholic liver disease, ALD) as well as non-alcoholic liver diseases. Metabolic liver disease comprises a spectrum of conditions characterized by hepatic fat deposition, e.g. excessive hepatic fat deposition, including particularly non-alcoholic fatty liver disease (NAFLD), more particularly non-alcoholic fatty liver (NAFL), non-alcoholic steatohepatitis (NASH) and/or NAFLD-associated liver fibrosis.

The spectrum of ALD in the context of the invention ranges from alcoholic fatty liver (steatosis) via alcoholic steatohepatitis (ASH) to hepatic fibrosis. Steatosis is the earliest stage of alcoholic liver disease and the most common alcohol-induced liver disorder. It is reversible, if the excessive alcohol intake is stopped in time. ASH is defined by the presence of fatty liver, an inflammatory infiltrate, which mainly consists of polymorphonuclear leukocytes, and hepatocellular damage.

Non-alcoholic liver diseases in the context of the invention are related to a metabolic dysregulation in the absence of excessive alcohol intake. A non-alcoholic liver disease of particular interest in the context of the invention is non-alcoholic fatty liver disease (NAFLD).

Non-alcoholic fatty liver disease (NAFLD) is the presence of hepatic steatosis in the absence of other causes for secondary hepatic fat accumulation (e.g., heavy alcohol consumption). Patients with non-alcoholic fatty liver disease (NAFLD) have hepatic steatosis, with or without inflammation, hepatocellular damage or fibrosis.

NAFLD is, in the context of the invention, subdivided into non-alcoholic fatty liver (NAFL), non-alcoholic steatohepatitis (NASH), and NAFLD-associated liver fibrosis. Thus, a patient having NAFLD according to the present invention has to be diagnosed with NAFL or NASH and/or NAFLD-associated liver fibrosis. Of note, fibrosis can typically be present to various extents in individuals with NASH. In NAFL, hepatic steatosis is present without evidence of hepatocellular ballooning and advanced inflammation, whereas in NASH, hepatic steatosis is associated with hepatic inflammation that may be histologically indistinguishable from alcoholic steatohepatitis. According to Ratziu et al (Gastroenterology 2016, vol. 150, pp. 1147-1159) and Kleiner and Bedossa (Gastroenterology 2015, vol. 149, pp. 1305-1308), NASH is distinguished from NAFL by the presence of hepatocyte ballooning with some degree of inflammation in addition to steatosis. Other terms that have been used to describe NASH include pseudoalcoholic hepatitis, alcohol-like hepatitis, fatty liver hepatitis, steatonecrosis, and diabetic hepatitis.

Liver fibrosis results from chronic damage to the liver in conjunction with the accumulation of extracellular matrix proteins, which is a characteristic of most types of chronic liver diseases. The main causes of liver fibrosis in industrialized countries include chronic HCV (hepatitis-C-virus) infection, alcohol abuse, and non-alcoholic steatohepatitis (NASH). The accumulation of extracellular matrix proteins distorts the hepatic architecture by forming a fibrous scar, and the subsequent development of nodules of regenerating hepatocytes defines cirrhosis (Bataller and Brenner, J Clin Invest. 2005, vol. 115, pp. 209-218).

Non-alcoholic steatohepatitis is a clinical entity characterized by liver biopsy findings that are identical to those seen in alcoholic hepatitis; patients with NASH, however, do not consume alcohol in quantities known to cause liver injury. Patients with NASH are typically obese, middle-aged or older, with asymptomatic hepatomegaly and are diabetic or hyperlipidemic and present with an unrelated medical problem. Analysis of liver biopsy specimens is the cornerstone of diagnosis; hepatic morphologic findings range from mild fatty degeneration and inflammation to cell degeneration, fibrosis, and cirrhosis with or without the presence of Mallory hyaline bodies.

NASH can be asymptomatic for a long period of time but may progress to liver cirrhosis or hepatocellular carcinoma (HCC). Accordingly, NAFLD-related liver cirrhosis and NAFLD-related hepatocellular carcinoma are also referred to herein as sequelae of NASH. The risk of progression from NASH to cirrhosis is particularly high in patients with advanced fibrosis. NAFLD-related cirrhosis is an important risk factor in the further development of the disease into NAFLD-related HCC. However, NAFLD-related HCC may also develop in NASH patients without cirrhosis.

Non-alcoholic fatty liver disease (NAFLD) is seen worldwide and is the most common metabolic liver disorder in Western industrialized countries, where the major risk factors for NAFLD, central obesity, type 2 diabetes mellitus, dyslipidemia, and metabolic syndrome are common. In the United States, studies report a prevalence of NAFLD of 10 to 46 percent, with most biopsy-based studies reporting a prevalence of NASH of 3 to 5 percent. Worldwide, NAFLD has a reported prevalence of 6 to 35 percent (median 20 percent) (Williams C D et al., Gastroenterology. 2011:140 (1):124-31; Vernon G et al., Alimwent Pharmacol Ther. 2011:34(3):274-85; Lazo M et al., Am J Epidemiol. 2013; 178(1):38-45). Estimates of prevalence of NAFLD in Asia-Pacific regions range from 5 to 30 percent, depending upon the population studied (Amarapurkar D N et al., J Gastroenterol Hepatol. 2007; 22:788-93).

Most patients are diagnosed with NAFLD in their 40s or 50s. Studies vary with regard to the sex distribution of NAFLD, with some suggesting it is more common in women and others suggesting it is more common in men. There appear to be ethnic differences in the prevalence of NASH. A study of hepatic triglyceride content in 2287 subjects from a US multi-ethnic, population-based sample found a higher prevalence of hepatic steatosis in Hispanics (45 percent) compared with whites (33 percent) or blacks (24 percent) (Browning J D et al., Hepatology. 2004; 40:1387-95). The higher prevalence in Hispanics was explained by a greater prevalence of obesity, though the lower prevalence in blacks persisted after controlling for body mass index and insulin sensitivity.

The pathogenesis of non-alcoholic fatty liver disease has not been fully elucidated. The most widely supported theory implicates insulin resistance as a key mechanism leading to hepatic steatosis, and perhaps also to steatohepatitis.

Most patients with non-alcoholic fatty liver disease (NAFLD) are asymptomatic, although some patients with non-alcoholic steatohepatitis (NASH) may complain of fatigue, malaise, and vague right upper abdominal discomfort. Patients are more likely to come to attention because laboratory testing revealed elevated liver aminotransferases or hepatic steatosis was detected incidentally on abdominal imaging. Once steatohepatitis has developed, the risk of cirrhosis is increased compared with simple steatosis. According to a recent publication from Bertot and Adams (Int J Mol Sci. 2016; 17(5):774-85), the progression rate of patients with NAFLD to NASH, from NAFLD to NASH with fibrosis, from NASH to NAFLD-related cirrhosis and from NASH with fibrosis to hepatocellular carcinoma is analyzed. There is a clearly increased risk of progression to cirrhosis in patients with NASH and about 25% of patients with NAFLD may progress to NASH within a 3-years time period. Once NASH is established, and depending on additional risk factors up to 38% percent of patients develop NAFLD related cirrhosis over time.

As mentioned above, it is particularly intended to use a compound or salt or solvate thereof of formula A or a pharmaceutical composition comprising such a compound in a method of preventing and/or treating non-alcoholic fatty liver disease (NAFLD). In certain embodiments, the disease state to be prevented and/or treated is non-alcoholic fatty liver (NAFL), non-alcoholic steatohepatitis (NASH) and/or NAFLD-associated liver fibrosis.

In certain preferred embodiments, the compound or salt or solvate thereof of formula A or the pharmaceutical composition comprising such a compound is for use in a method of preventing and/or treating non-alcoholic steatohepatitis (NASH). NASH may or may not be associated with different stages of liver fibrosis.

The preferred means of accurately assessing distinguishing NASH from steatosis with inflammation is currently histological evaluation of liver biopsies. In 2005, the Pathology Committee of the NASH Clinical Research Network (CRN) developed the so-called "NAFLD activity score (NAS)" for use in clinical trials (Kleiner et al., Hepatology 2005, vol. 41, pp. 1313-1321). Other scoring systems may also be used to diagnose NAFLD and the severity of its components.

The NAS specifically includes features of active injury that are potentially reversible in the short term. The NAS is defined as the unweighted sum of the subscores for (i) steatosis, (ii) lobular inflammation and (iii) hepatocellular ballooning. Each subscore is graded semi-quantitatively as described in the following Table 2.

TABLE 2

Definition of NAS subscores

| Subscore histological feature | definition | score |
|---|---|---|
| | steatosis (0-3) | |
| grade | low-to medium-power evaluation of parenchymal involvement by steatosis (% of cells) | |
| | <5% | 0 |
| | 5%-33% | 1 |
| | >33%-66% | 2 |
| | >66% | 3 |
| | lobular inflammation (0-3) | |
| | overall assessment of all inflammatory foci | |
| | no foci | 0 |
| | 1 to <2 foci per 200x field | 1 |
| | 2-4 foci per 200x field | 2 |
| | >4 foci per 200x field | 3 |
| | hepatocellular ballooning (0-2) | |
| | no ballooned cells | 0 |
| | few ballooned cells (rare but definite ballooned hepatocytes, cases that are diagnostically borderline included) | 1 |
| | many ballooned cells/prominent ballooning | 2 |

Usually, NAFLD is defined by the presence of steatosis in >5% of hepatocytes, NASH by the presence, in addition, of hepatocellular ballooning of any degree and lobular inflammatory infiltrates of any amount (Bedossa et al., Hepatology 2015, vol. 56, pp. 1751-1759).

Diagnosis of NAFLD and NASH according to the present invention is described in the following Table 3:

TABLE 3

Diagnostic algorithm for NAFL versus NASH according to NAS subscores

| steatosis | (hepatocyte) ballooning | (lobular) inflammation | diagnosis |
|---|---|---|---|
| 0 | 0, 1, 2 | 0, 1, 2, 3 | No NAFLD |
| 1, 2, 3 | 0 | 0 | NAFL |
| 1, 2, 3 | 0 | 1 | NAFL |
| 1, 2, 3 | 0 | 2 | NASH |
| 1, 2, 3 | 0 | 3 | NASH |
| 1, 2, 3 | 1 | 0 | NASH |
| 1, 2, 3 | 1 | 1 | NASH |
| 1, 2, 3 | 1 | 2 | NASH |
| 1, 2, 3 | 1 | 3 | NASH |
| 1, 2, 3 | 2 | 0 | NASH |
| 1, 2, 3 | 2 | 1 | NASH |
| 1, 2, 3 | 2 | 2 | NASH |
| 1, 2, 3 | 2 | 3 | NASH |

Accordingly, in the context of the present invention, a patient is diagnosed as suffering from NAFLD, if at least the subscore for steatosis (sometimes also referred to as the "steatosis subscore" or simply "steatosis score" herein) is 1. NASH can be discriminated from NAFL or simple steatosis by the presence of hepatocyte ballooning (sometimes also referred to as the "ballooning subscore" or simply "ballooning score" herein) with or without some degree of inflammation (sometimes also referred to as the "inflammation subscore" or simply "inflammation score" herein). In this context, NASH resolution has been defined as the disappearance of ballooning (subscore=0), together with either disappearance of lobular inflammation or the persistence of mild lobular inflammation only (subscore=0 or 1) (Kleiner and Bedossa, Gastroenterology 2015, vol 149, pp. 1305-1308). This definition was used for the diagnostic algorithm described in Table 3.

To assess efficacy of the compounds of the invention, not only the NAS, but also the fibrosis score is determined. The fibrosis score may, for example, be determined according to Kleiner et al. (Hepatology 2005, vol. 41, pp. 1313-1321; also referred herein as the "Kleiner fibrosis score"), summarized in the following Table 4.

TABLE 4

Definition of the Kleiner fibrosis score

| Fibrosis | comments | score |
| --- | --- | --- |
| none | | 0 |
| portal/periportal | mild fibrosis | 1 |
| perisinusoidal and portal/periportal | moderate fibrosis between portal areas, but without destruction of the lobular structure | 2 |
| bridging fibrosis | fibrotic bridging between portal areas and between portal areas and center veins | 3 |
| cirrhosis | additionally pseudo-lobules formed | 4 |

Whereas the NAS determines the extent of NAFL and NASH (higher score means higher disease activity), the Kleiner fibrosis score determines the extent of fibrosis progression. A decrease in NAS only is relevant if fibrosis does not further progress. Therefore, a positive response to treatment exists, if no worsening (i.e. increase) or an improvement (lower score) in NAS, in particular disappearance of hepatocyte ballooning (ballooning score=0), is present in the absence of worsening (i.e. increase) of the Kleiner fibrosis score.

In the context of the invention, it is in principle possible to perform the intended medical uses directly with compounds of formula A or salts or solvates thereof alone. However, the compounds of formula A or salts or solvates thereof are usually provided in a pharmaceutical composition as defined above.

In some embodiments, pharmaceutical compositions comprising a compound of formula A are for use in a method of treating NAFLD, wherein a patient is considered as suffering from NAFLD, when the steatosis subscore is >0.

In some embodiments, pharmaceutical compositions comprising a compound of formula A are for use in a method of treating NAFL, wherein a patient is considered as suffering from NAFL, when steatosis is present (subscore>0), but the ballooning subscore is 0 and the inflammation subscore is 0 or 1. In some embodiments, the patients have a Kleiner fibrosis score of 0 (NAFLD without fibrosis), whereas in other embodiments, the patients have a Kleiner fibrosis score of >0 and <4 (NAFLD with fibrosis).

It is particularly envisaged that pharmaceutical compositions comprising a compound of formula A are for use in a method of treating human patients. These human patients are particularly adult patients (i.e. >18 years of age), more particularly between >18 and <75 years of age. Further, the patients particularly have a body mass index (BMI) of ≥25 more particularly between ≥25 and ≤45 kg/m². In certain embodiments, the patients are ≥18 years of age and have a BMI ≥25.

In some embodiments, pharmaceutical compositions comprising compounds of formula A are for use in a method of treating NASH, wherein a patient, particularly a human patient, is diagnosed as having NASH, if there is a presence of steatosis and hepatocyte ballooning (each subscore>0) and any degree of inflammation (subscore 0-3), or, alternatively, steatosis (subscore>0) and advanced inflammation (subscore>1) in the absence of hepatocyte ballooning (subscore=0), with a Kleiner fibrosis score of <4. In some embodiments, the patients have a Kleiner fibrosis score of 0 (NASH without fibrosis), whereas in other embodiments, the patients have a Kleiner fibrosis score of >0 and <4 (NASH with fibrosis).

According to certain preferred embodiments, the invention relates to a compound of formula A or a salt or solvate thereof, particularly SEQ ID NO.: 1, for use in a method of treating NASH in a human patient, wherein the patient is considered as suffering from NASH, when, at the onset of treatment, (i) steatosis and hepatocyte ballooning scores are >0, or, in the absence of hepatocyte ballooning, steatosis score is >0 and inflammation score is >1, and (ii) a Kleiner fibrosis score of >0 and <4 is determined.

According to certain embodiments, a treatment of NASH is considered successful, if the NAS decreases and the Kleiner fibrosis score does not increase.

According to other embodiments, a treatment of NASH is considered successful, if the NAS does not increase and the Kleiner fibrosis score decreases.

It is also encompassed by the invention to use compounds of general formula A or salts or solvates thereof in methods of preventing and/or treating, particularly treating, liver cirrhosis. Cirrhosis may be caused by chronic alcohol abuse or by a chronic viral hepatitis (e.g., hepatitis B or hepatitis C). Also, non-alcoholic fatty liver (NAFL) or NASH can progress to liver cirrhosis (NAFLD-related liver cirrhosis). Complications of cirrhosis may include variceal hemorrhage, ascites, spontaneous bacterial peritonitis, hepatic encephalopathy, hepatocellular carcinoma, hepatorenal syndrome, and hepatopulmonary syndrome. These complications are associated with a high socio-economic burden. Accordingly, in some embodiments, compounds of formula A or salts or solvates thereof are for use in a method of treating liver cirrhosis, particularly NAFLD-related liver cirrhosis, wherein a patient, particularly a human patient, is diagnosed as having liver cirrhosis, when a Kleiner fibrosis score of 4 is determined.

It is further encompassed by the invention to use compounds of general formula A or salts or solvates thereof in methods of preventing and/or treating, particularly treating, hepatocellular carcinoma, also referred to as hepatocellular cancer and abbreviated HCC. HCC is mainly caused by liver cirrhosis, but also patients with hepatitis B or C are at high risk of developing develop HCC, without cirrhosis. Accordingly, in some embodiments, compounds of formula A or salts or solvates thereof are for use in a method of treating HCC, particularly NAFLD-related HCC. Diagnostic criteria and algorithm for HCC have been published by the American Association for the Study of Liver Diseases (AASLD) (Bruix J, et al. Hepatology. 2011; 53(3):1020-22).

A yet further aspect of the invention is to use dual GLP-1/glucagon receptor agonists of formula A in the parallel prevention or treatment, particularly treatment, of NASH and at least one additional pathologic condition or risk factor. Pathologic conditions and risk factors suitable to be simultaneously treated with NASH include, but are not limited to, obesity, type 2 diabetes mellitus, dyslipidemia and other metabolic disorders. According to some embodiments, a compound of formula A or a salt or solvate thereof is for use in simultaneously treating NASH and type 2 diabetes mellitus. According to other embodiments, a compound of formula A or a salt or solvate thereof is for use in simultaneously treating NASH and obesity. According to yet further embodiments, a compound of formula A or a salt or solvate thereof is for use in simultaneously treating NASH and type 2 diabetes mellitus and obesity.

A standard criterion to define a patient as being obese is a body mass index (BMI) of at least 30, but obesity may also be determined according to other suitable criteria. Accordingly, in some embodiments of the present application, a patient is considered as being obese, when a BMI of 30 is determined.

In the context of some embodiments of the present invention, a patient is considered as suffering from type 2 diabetes mellitus, when a fasting plasma glucose concentration of mmol/l is determined. In some embodiments a patient is considered as suffering from type 2 diabetes mellitus, when a plasma glucose concentration of 11.1 mmol/l in a glucose tolerance test two hours after an oral 75 g glucose load is determined. In some embodiments a patient is considered as suffering from type 2 diabetes mellitus, when a glycated hemoglobin HbA1c value of ≥48 mmol/mol (6.5%) is determined. It is possible that more than one of the above criteria is met by a patient suffering from type 2 diabetes mellitus, but fulfilment of one criterion is considered sufficient for diagnosis in the context of the invention. By contrast, a patient is considered as not suffering from diabetes, if none of the above-defined criteria is met.

Thus, according to some embodiments of the invention, a compound of formula A or a salt or solvate thereof, or a pharmaceutical composition comprising a compound of formula A or a salt or solvate thereof is for use in treating NASH in patients suffering from NASH, but not suffering from type 2 diabetes mellitus and obesity. This patient group may be defined as (i) showing steatosis (score>0) and hepatocyte ballooning (score>0) and any degree of inflammation (score 0-3), or, alternatively, steatosis (score>0) and advanced inflammation (score>1) in the absence of hepatocyte ballooning (score=0), each with a Kleiner fibrosis score of <4 (NASH criteria);

(ii) having fasting plasma glucose concentration of <7 mmol/l and a plasma glucose concentration of <11.1 mmol/l in a glucose tolerance test two hours after an oral 75 g glucose load and a glycated hemoglobin HbA1c value of <48 mmol/mol (<6.5%) (type 2 diabetes mellitus criteria);

(iii) having a BMI <30, i.e. not within the obese range (obesity criterion).

According to further embodiments of the invention, a compound of formula A or a salt or solvate thereof, or a pharmaceutical composition comprising a compound of formula A or a salt or solvate thereof is for use in treating NASH in patients suffering from NASH and at the same time suffering from type 2 diabetes mellitus, but not from obesity. This patient group may be defined as (i) showing steatosis (score>0) and hepatocyte ballooning (score>0) and any degree of inflammation (score 0-3), or, alternatively, steatosis (score>0) and advanced inflammation (score>1) in the absence of hepatocyte ballooning (score=0), each with a Kleiner fibrosis score of <4 (NASH criteria);

(ii) having fasting plasma glucose concentration of mmol/l or/and a plasma glucose concentration of ≥11.1 mmol/l in a glucose tolerance test two hours after an oral 75 g glucose load or/and a glycated hemoglobin HbA1c value of ≥48 mmol/mol (≥6.5%) (diabetes type 2 criteria);

(iii) having a BMI<30, i.e. not within the obese range (obesity criterion).

According to further embodiments of the invention, a compound of formula A or a salt or solvate thereof, or a pharmaceutical composition comprising a compound of formula A or a salt or solvate thereof is for use in treating NASH in patients suffering from NASH and at the same time suffering from obesity, but not from type 2 diabetes mellitus. This patient group may be defined as (i) showing steatosis (score>0) and hepatocyte ballooning (score>0) and any degree of inflammation (score 0-3), or, alternatively, steatosis (score>0) and advanced inflammation (score>1) in the absence of hepatocyte ballooning (score=0), each with a Kleiner fibrosis score of <4 (NASH criteria);

(ii) having fasting plasma glucose concentration of <7 mmol/l and a plasma glucose concentration of <11.1 mmol/l in a glucose tolerance test two hours after an oral 75 g glucose load and a glycated hemoglobin HbA1c value of <48 mmol/mol (<6.5%) (diabetes type 2 criteria);

(iii) having a BMI 30, i.e. within the obese range (obesity criterion).

According to yet further embodiments of the invention, a compound of formula A or a salt or solvate thereof, or a pharmaceutical composition comprising a compound of formula A or a salt or solvate thereof is for use in treating NASH in patients suffering from NASH and at the same time suffering from both type 2 diabetes mellitus and obesity. This patient group may be defined as (i) showing steatosis (score>0) and hepatocyte ballooning (score>0) and any degree of inflammation (score 0-3), or, alternatively, steatosis and advanced inflammation (score>1) in the absence of hepatocyte ballooning (score=0), each with a Kleiner fibrosis score of <4 (NASH criteria);

(ii) having fasting plasma glucose concentration of mmol/l or/and a plasma glucose concentration of ≥11.1 mmol/l in a glucose tolerance test two hours after an oral 75 g glucose load or/and a glycated hemoglobin HbA1c value of ≥48 mmol/mol (≥6.5%) (diabetes type 2 criteria);

(iii) having a BMI≥30, i.e. within the obese range (obesity criterion).

Furthermore, it is encompassed by the invention that NASH or NASH and at least one additional pathological risk factor are treated by a pharmaceutical composition comprising a compound of formula A in combination with one or more further therapeutically active ingredients. The further therapeutically active ingredient or ingredients may be administered separately, contemporaneously sequentially, at different dose frequencies or via different routes of administration.

FIGURE LEGENDS

FIGS. 1A-1F. Effect of treatment with compound 2 (SEQ ID NO.: 2) at a dose of 10 µg/kg twice daily over eight weeks in mice with AMLN-diet-induced NASH, compared to vehicle-treated control animals on the same diet. (FIG. 1A) Body weight at baseline and after 52 days of treatment; (FIG. 1B) Overall NAFLD activity score after termination of treatment on day 56; (FIG. 1C) Individual change in NAFLD activity score vs. pre-biopsy before start of treatment; (FIG. 1D) Individual components of the NAFLD activity score (hepatic steatosis, lobular inflammation, hepatocyte ballooning) at end of the study for compound-vs vehicle-treated animals; (FIG. 1E) Fibrosis score at baseline and after eight weeks of treatment. (FIG. 1F) Change in fibrosis score vs. baseline.

FIGS. 2A-2E. Effect of treatment with compound 3 (SEQ ID NO.: 3) at a dose of 30 µg/kg once daily, liraglutide (SEQ ID NO.: 4) at a dose of 200 µg/kg once daily over eight weeks in mice with AMLN-diet-induced NASH, compared to vehicle-treated control animals on the same diet. (FIG. 2A) Body weight at baseline and after 56 days of treatment; (FIG. 2B) Overall NAFLD activity score after termination of treatment on day 56; (FIG. 2C) Individual change in NAFLD activity score vs. pre-biopsy before start of treatment; (FIG. 2D) Individual components of the NAFLD activity score (hepatic steatosis, lobular inflammation, hepatocyte ballooning) at end of the study for compound-vs vehicle-treated animals; (FIG. 2E) Change in fibrosis score vs. baseline.

FIGS. 3A-3E. Effect of treatment with compound 1 (SEQ ID NO.: 1) at doses of 10 and 30 µg/kg twice daily, liraglutide (SEQ ID NO.: 4) at a dose of 100 µg/kg twice daily over eight weeks in mice with AMLN-diet-induced NASH, compared to vehicle-treated control animals on the same diet. (FIG. 3A) Body weight at baseline and after 55 days of treatment; (FIG. 3B) Overall NAFLD activity score after termination of treatment on day 56; (FIG. 3C) Individual change in NAFLD activity score vs. pre-biopsy before start of treatment; (FIG. 3D) Individual components of the NAFLD activity score (hepatic steatosis, lobular inflammation, hepatocyte ballooning) at end of the study for compound-vs vehicle-treated animals; (FIG. 3E) Change in fibrosis score vs. baseline.

METHODS

Test compounds were investigated in a mouse model of NASH (murine diet-induced NASH model) as described in Kristiansen et al (World Journal of Hepatology 2016, vol. 8, pp. 673-684). C57BL/6J mice were given ad libitum access to a diet (D09100301, Research Diet, United States) high in fat (40%, of these 18% trans-fat), carbohydrates (40%, of these 20% fructose) and cholesterol (2%) that has previously been described as AMLN diet (Clapper et al., Am J Physiol Gastrointest Liver Physiol 2013, vol. 305, pp. G483-G495). A control group was kept on regular rodent chow (Altromin 1324, Brogaarden, Denmark).

After 26 weeks on the diet, a liver biopsy was performed for histological assessment of NASH and fibrosis at baseline. For this purpose, about 100 mg liver tissue were collected from the left lateral lobe, fixed overnight in 4% paraformaldehyde, paraffin-embedded and sectioned (3 µm thickness). For histological assessment, sections were stained with hematoxylin, eosin or Sirius Red and followed by analysis with Visiomorph software (Visiopharm, Denmark). Histological scoring was performed by a pathologist blinded to the study. NAFLD activity score and fibrosis score were determined according to the clinical criteria outlined by Kleiner et al (Hepatology 2005, vol. 14, pp. 1313-1321).

Animals were randomized into different treatment groups according to body weight and extent of fibrosis. Treatment period was eight weeks during which animals remained on the AMLN diet. Compounds were given by once-daily or twice-daily subcutaneous injection. Vehicle-treated animals on AMLN diet and non-treated animals on regular rodent chow were included as controls. Group sizes were between 8 and 14 animals.

After treatment, terminal liver samples were collected and analysed as for the pre-biopsy.

The invention is further illustrated by the following examples.

EXAMPLES

Example 1: Investigation of Efficacy of Dual GLP-1/Glucagon Receptor Agonists in a Murine Diet-Induced Nash Model Dual-agonistic GLP1R/GCGR agonistic peptides were investigated in a murine model of NASH as described in the methods section. Treatment duration was eight weeks over which animals remained on the NASH-inducing AMLN diet. The GLP1R-specific agonist liraglutide (SEQ ID NO.: 4) was included as a reference compound.

Results:

Three GLP1R/GCGR dual agonistic peptides (SEQ ID NO.: 1; SEQ ID NO.: 2 and SEQ ID NO.: 3) were investigated in the murine diet-induced NASH model.

In the diet-induced murine NASH model, compounds were administered at the following doses (all via subcutaneous injections): SEQ ID NO.: 2 10 µg/kg b.i.d., SEQ ID NO.:3 30 µg/kg q.d. in comparison to liraglutide (SEQ ID NO.: 4) at 200 µg/kg q.d., SEQ ID NO.: 1 10 µg/kg b.i.d. or 30 µg/kg b.i.d. in comparison to liraglutide (SEQ ID NO.: 4) at 100 µg/kg b.i.d.

The treatment effects of the compound of SEQ ID NO.: 2 are summarized in FIGS. 1A-1F, those of the compound of SEQ ID NO.: 3 in comparison to liraglutide (SEQ ID NO.: 4) in FIGS. 2A-2E and those of the compound of SEQ ID NO.: 1 in comparison to liraglutide (SEQ ID NO.: 4) in FIGS. 3A-3E.

After 26 weeks on the AMLN diet, the average body weight of the animals in the groups assigned to different treatments was between 36 and 40 grams, whereas mice that had remained on normal rodent chow weighed between 29 and 32 grams. Over the eight-week treatment period, vehicle-treated mice gained up to 2 grams of body weight. In contrast, animals that received liraglutide or GLP1R/GCGR dual agonists showed significant weight loss.

For SEQ ID NO.: 2, weight loss was 2.8 gram (7.7%) vs baseline whereas vehicle-treated animals in the same study gained 2.1 grams (5.6%), i.e. weight loss vs vehicle was 4.9 grams or 13.5% of body weight at baseline (FIG. 1A).

Upon eight-week administration of SEQ ID NO.: 3, animals lost 3.9 grams (10.5%) whereas mice given vehicle injections gained 1.1 grams (3.0%). In the same study, injection of liraglutide (SEQ ID NO.: 4) over eight weeks was associated with a weight loss of 3.2 gram (8.7% of body weight at baseline, FIG. 2A).

Animals treated with either 10 µg/kg or 30 µg/kg SEQ ID NO.: 1 twice daily over eight weeks lost 3.0 grams (8.5%) or 3.9 grams (11.4%) respectively. In this study, vehicle-treated mice gained 0.5 grams (1.3%) whereas animals treated with 100 µg/kg liraglutide (SEQ ID NO.: 4) twice daily lost 2.4 grams (6.4%, FIG. 3A)).

While body weight change was highly significantly different from vehicle for liraglutide and all dual GLP1R/GCGR agonists tested ($p<0.001$), it was not significantly different between the dual agonists and liraglutide tested in the same studies.

Figure 1B:
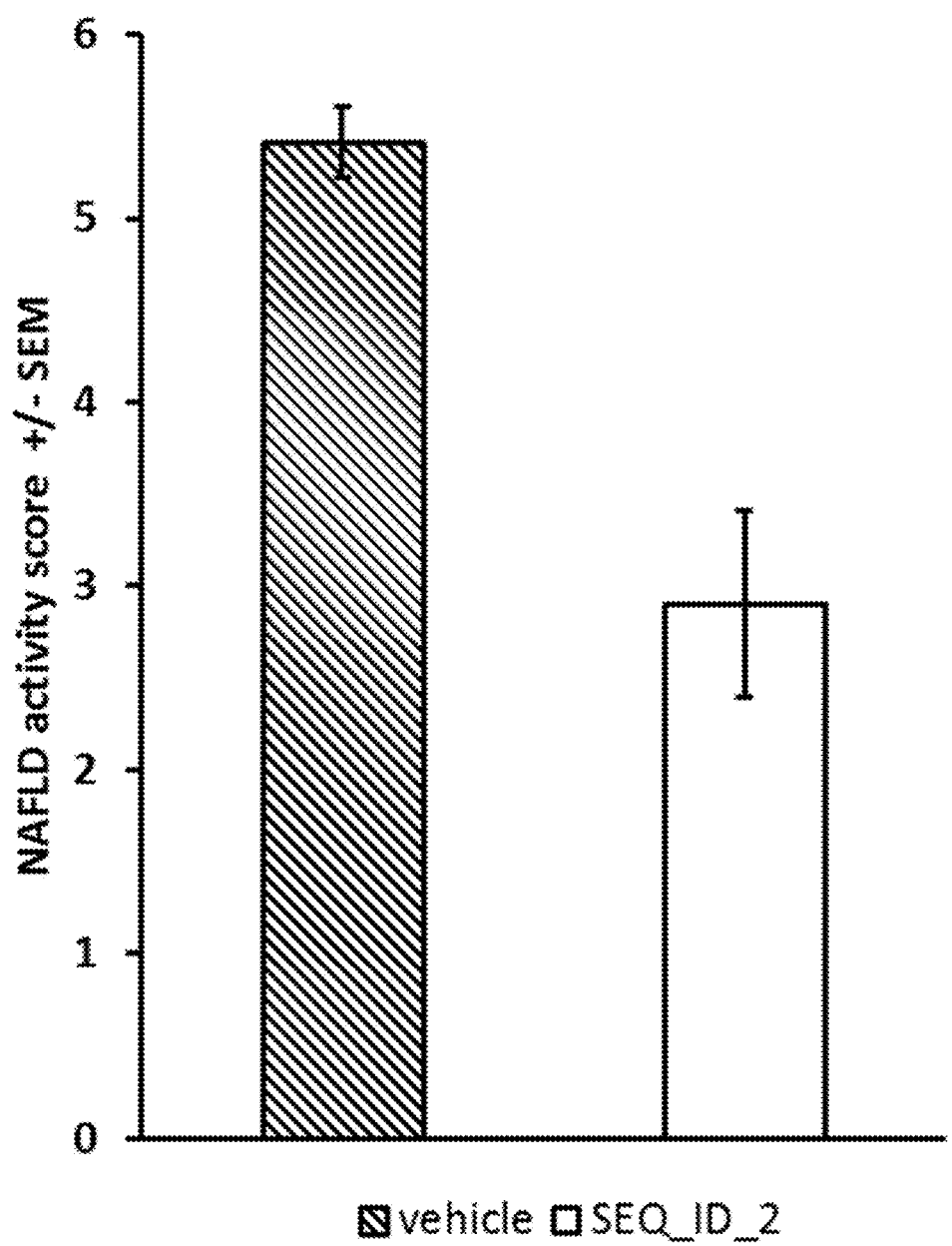
Figure 1C:
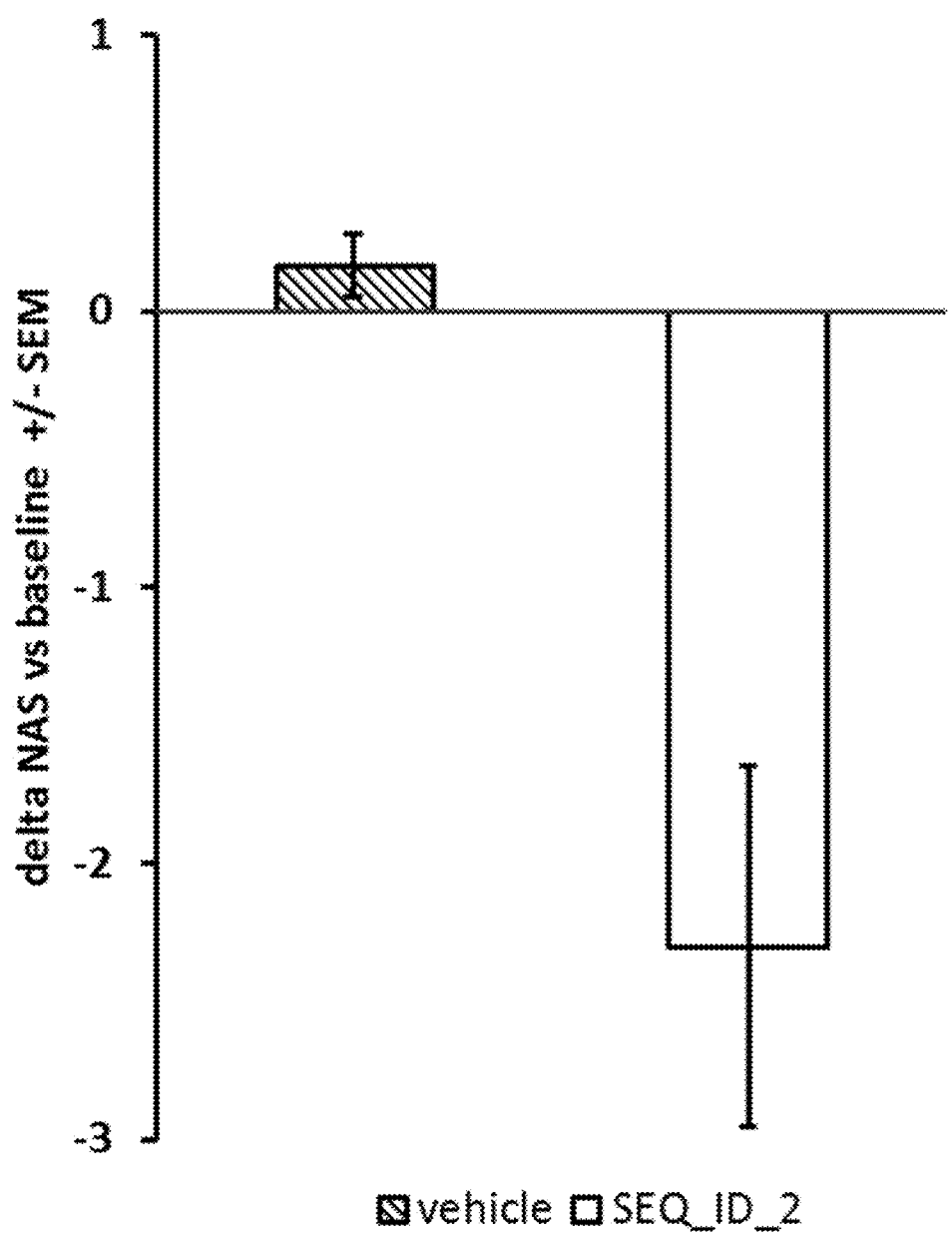
Figure 1D:
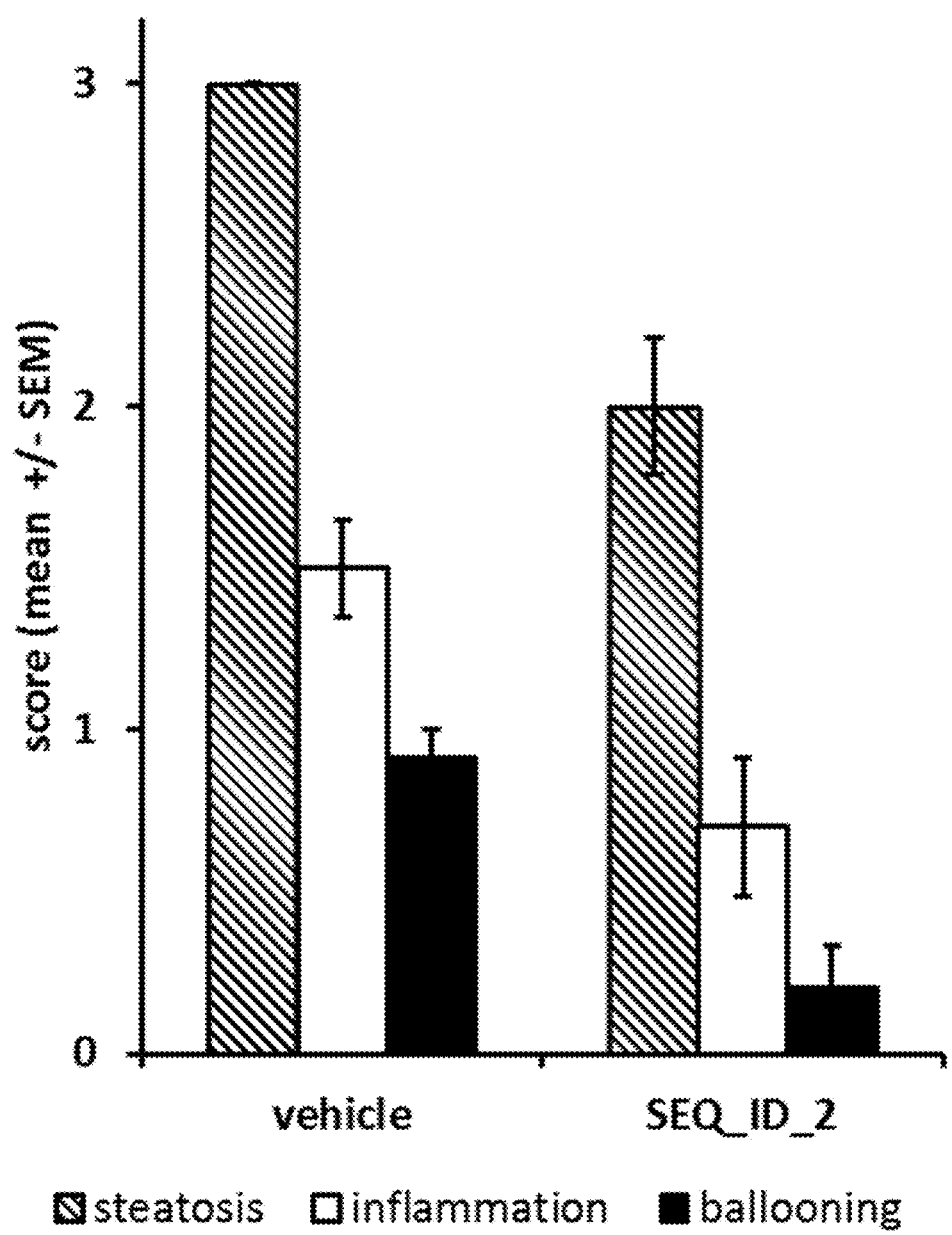
Figure 1E:
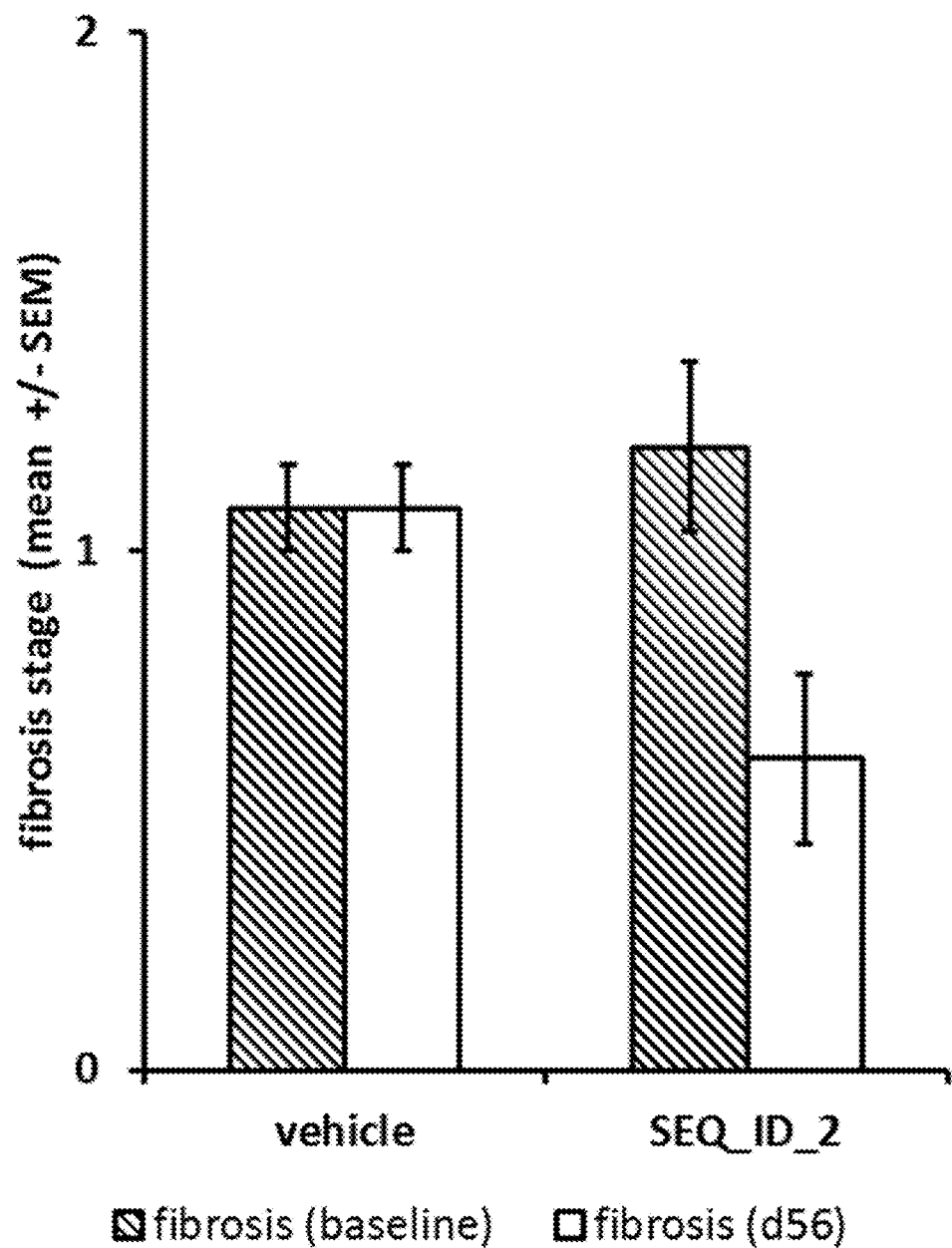
Figure 1F:
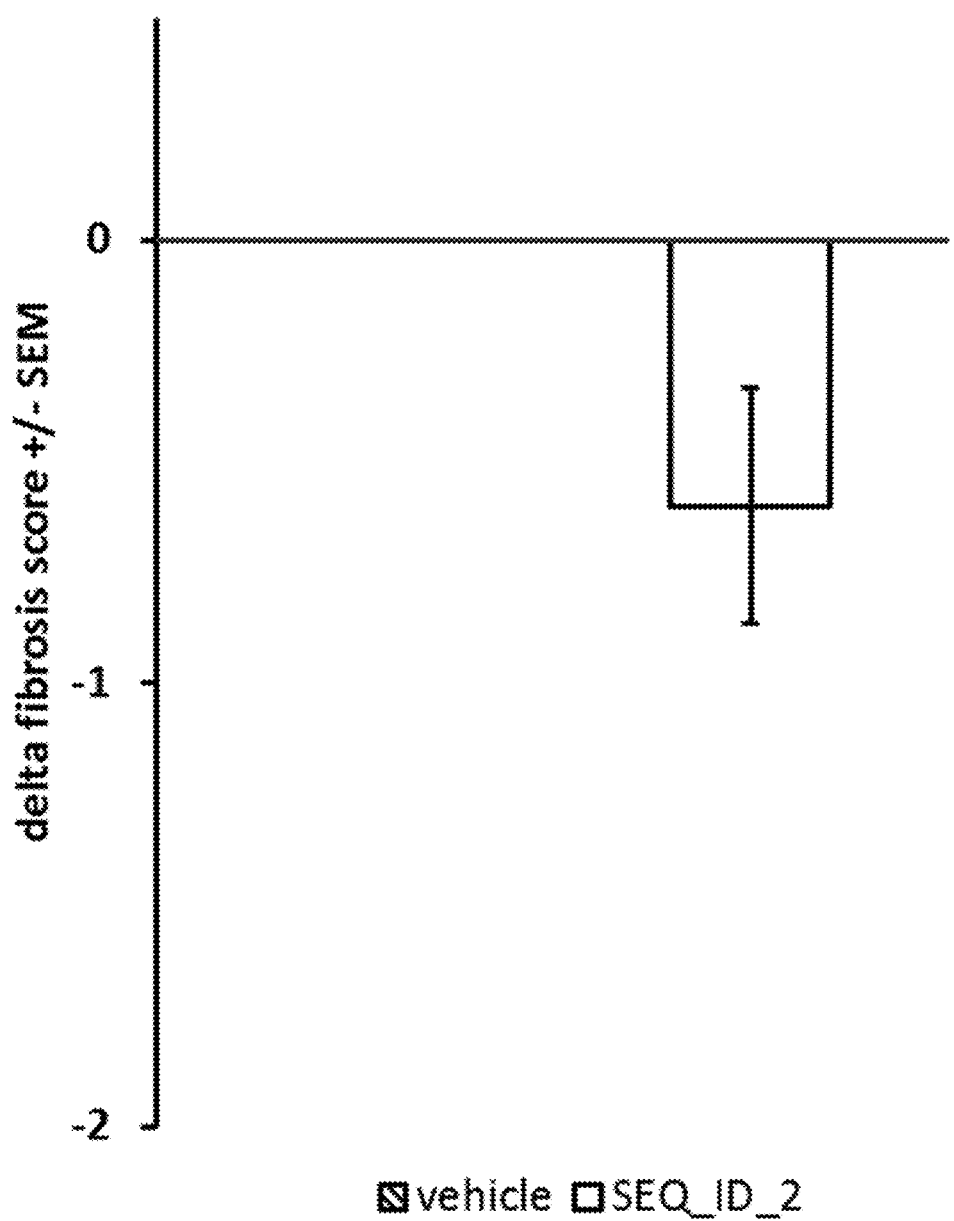

Treatment with the compound of SEQ ID NO.: 2 (10 µg/kg b.i.d) resulted in a reduction in NAFLD activity score (NAS) by 2.3 points whereas there was a slight increase by 0.2 points for the vehicle-treated group (FIGS. 1A-1C). A reduction in score was seen for all three components of NAS, i.e. the steatosis, inflammation and hepatocyte ballooning scores (FIG. 1D). Also, there was an improvement in fibrosis compared to the vehicle group: While the mean fibrosis stage did not change in the vehicle group, it decreased from 1.2 to 0.6 in the group treated with the compound of SEQ ID NO.: 2 (FIG. 1A1E).

Figure 2A:
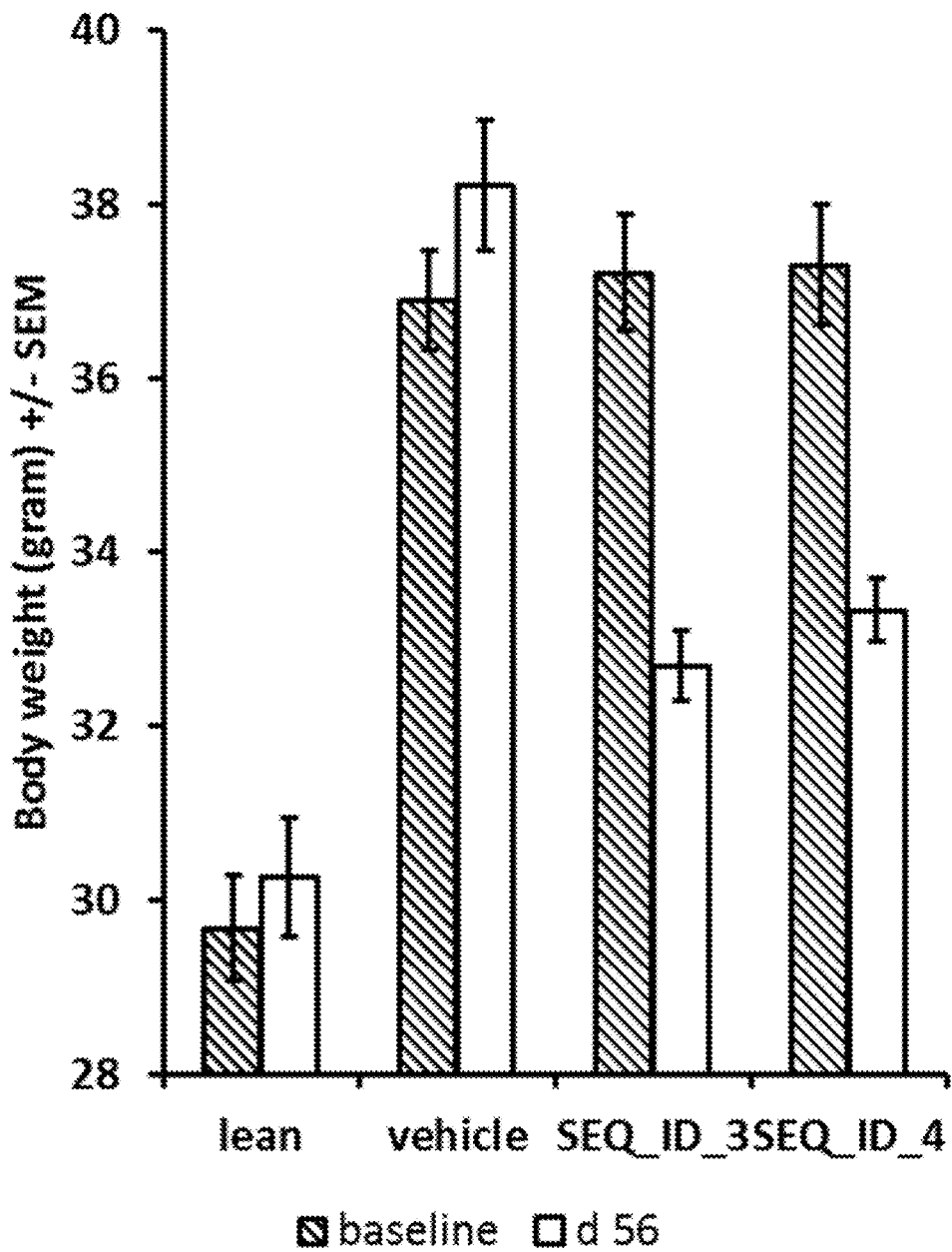
Figure 2B:
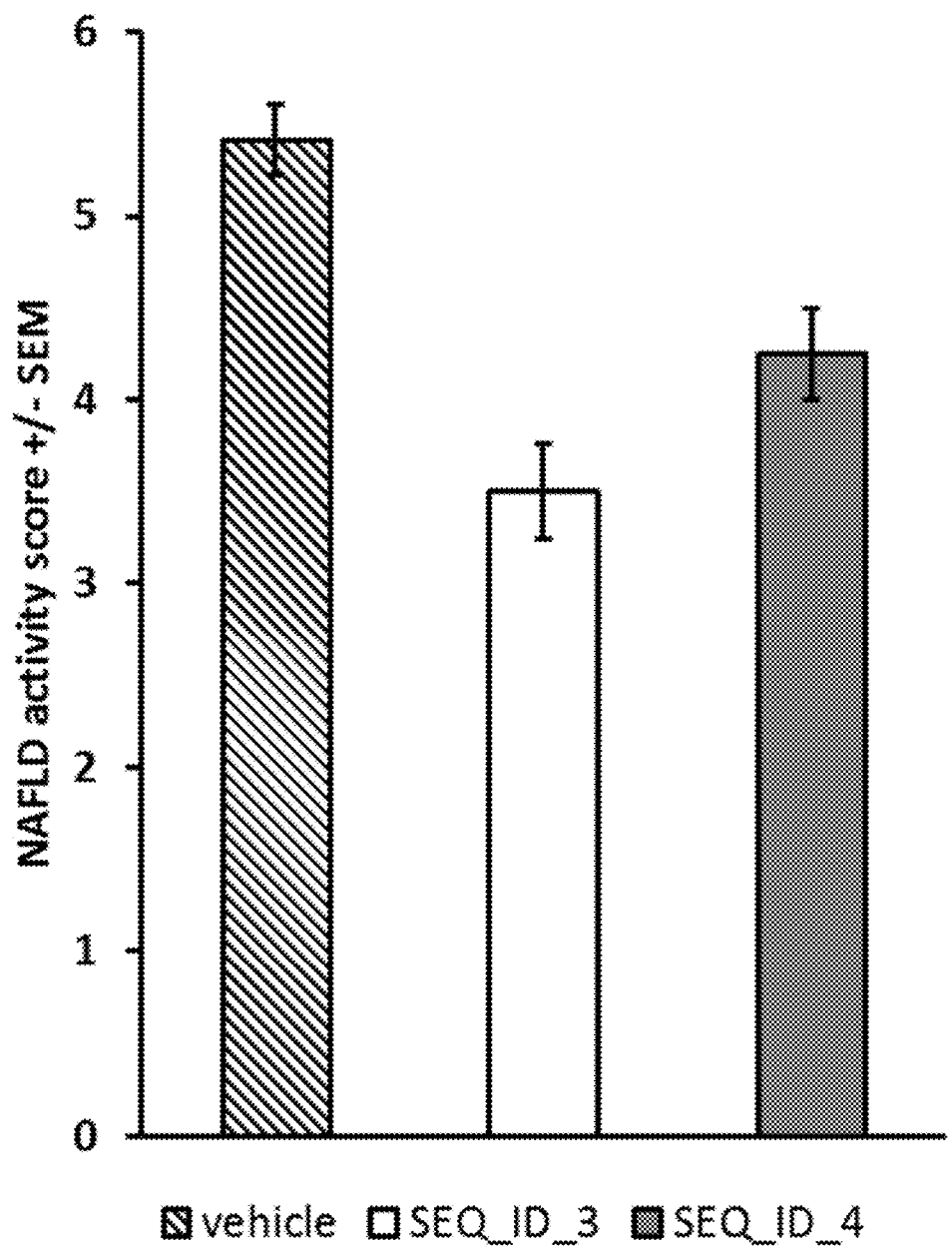
Figure 2C:
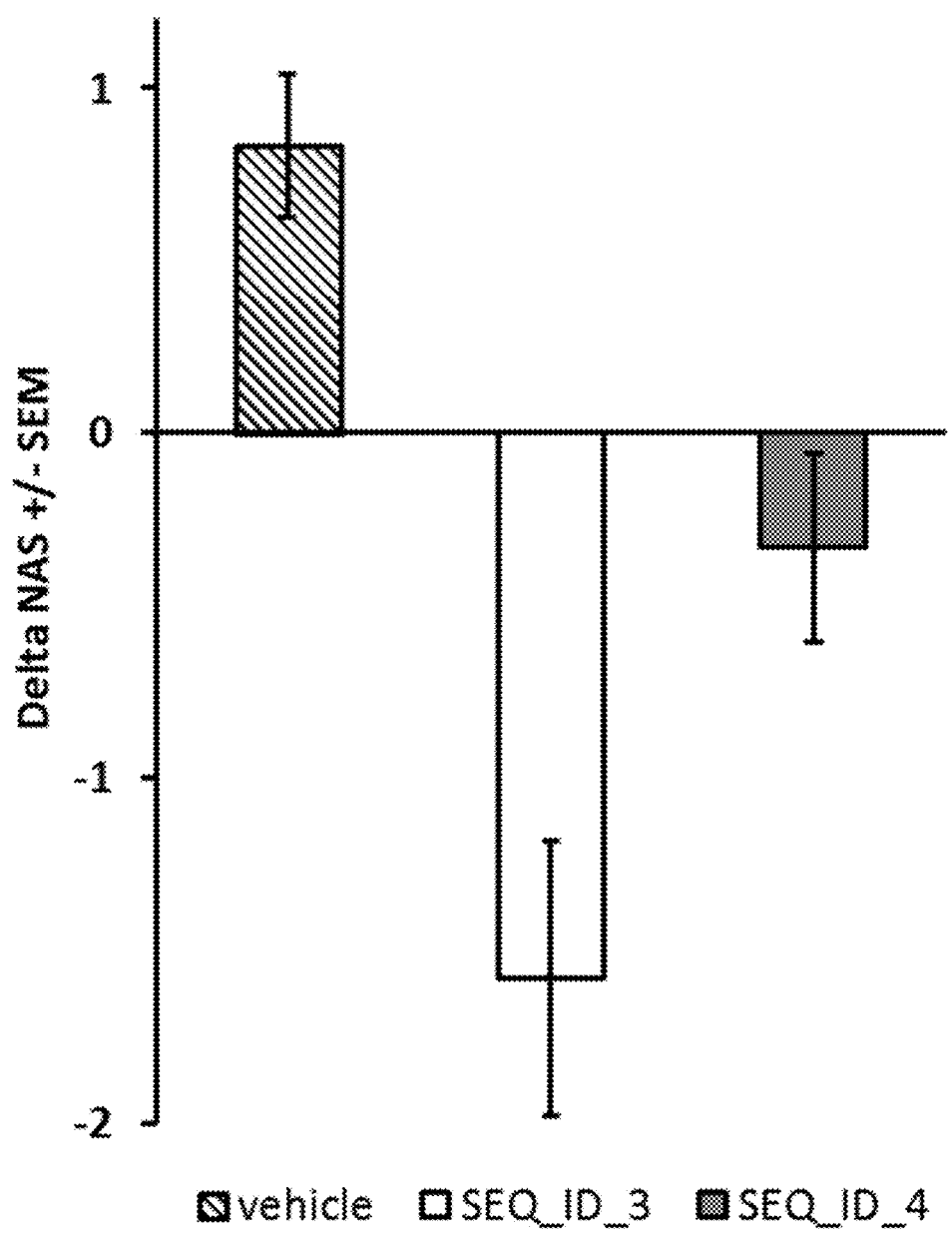
Figure 2D:
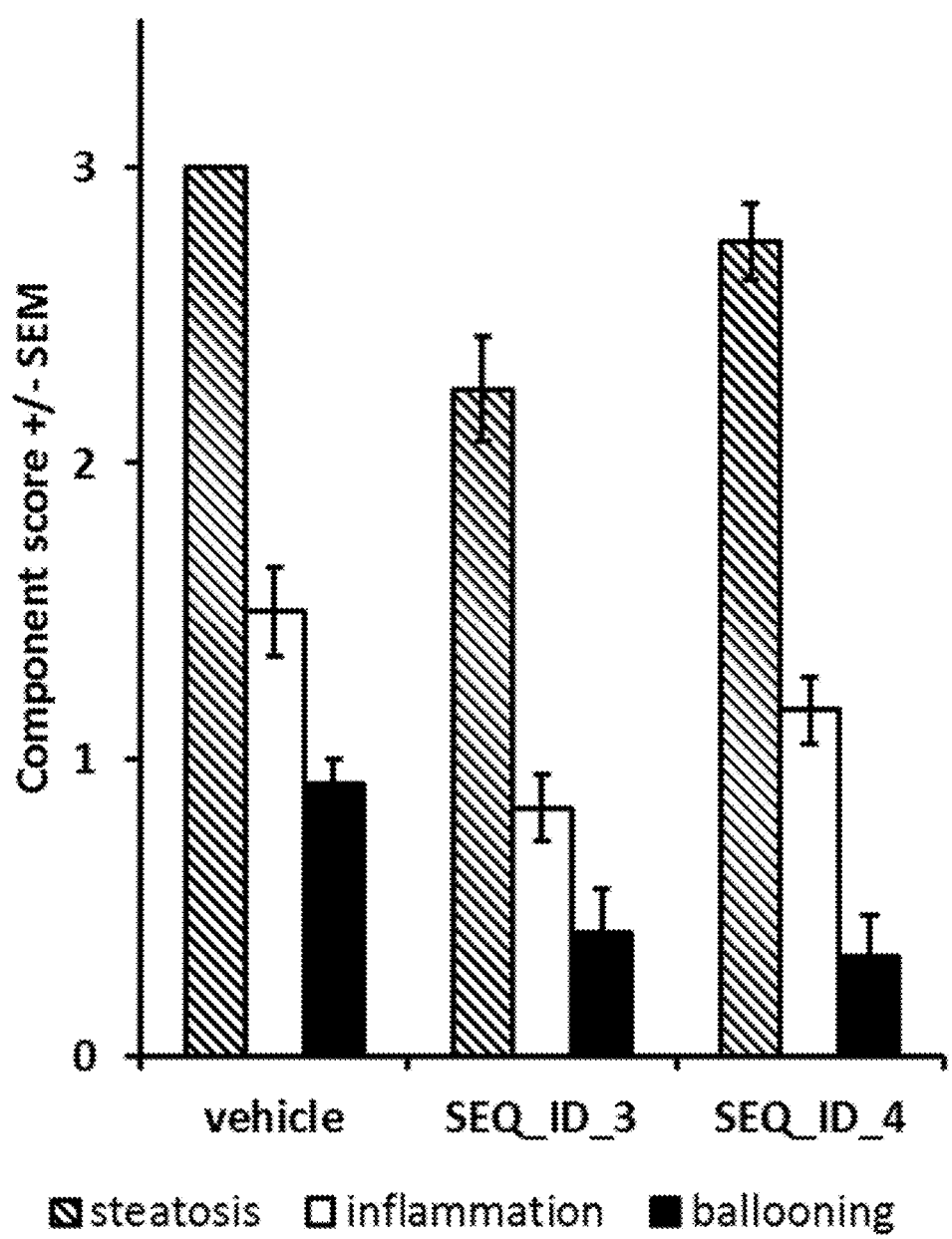
Figure 2E:
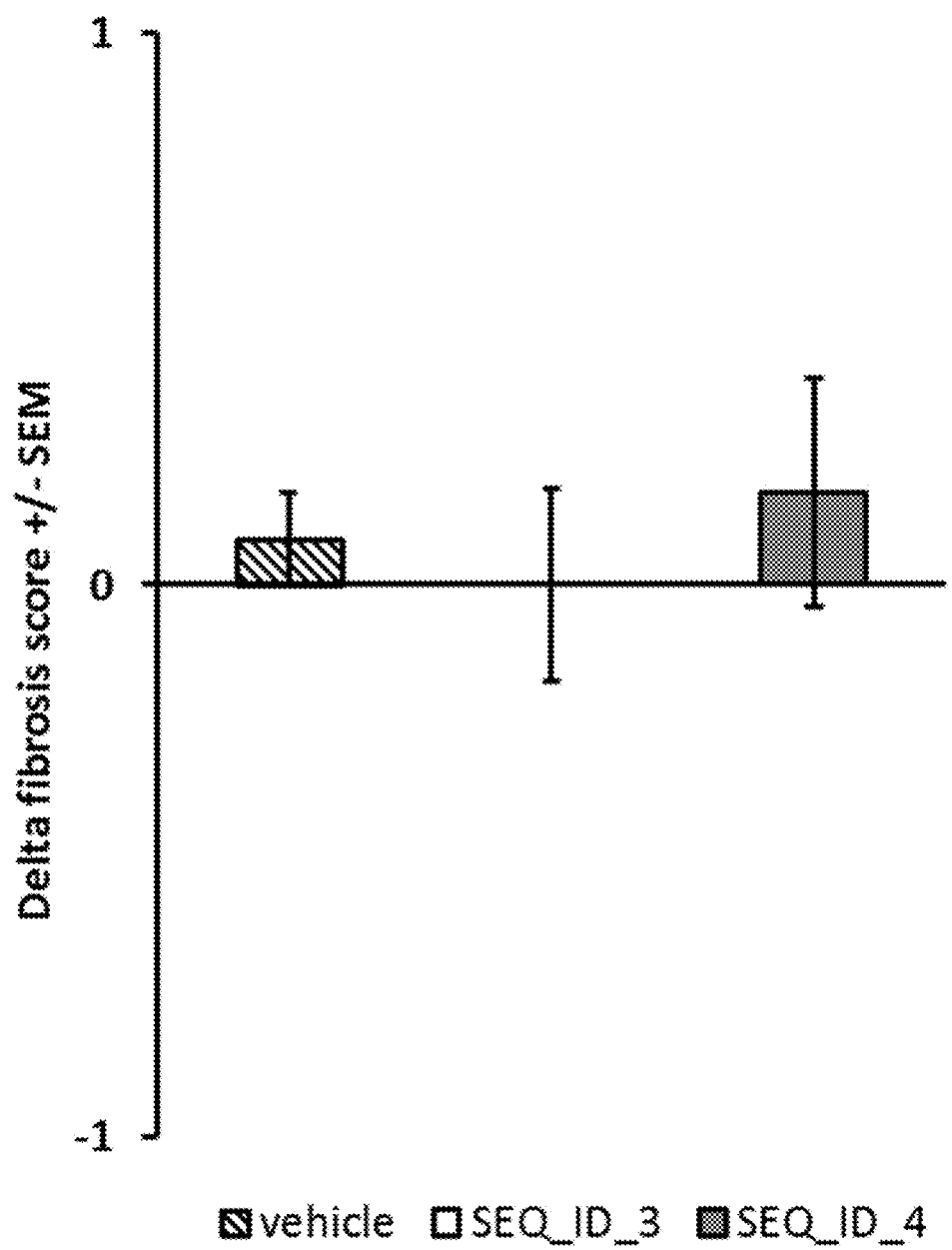

Treatment with the compound of SEQ ID NO.: 3 (30 μg/kg q.d.) or liraglutide (200 μg/kg q.d.) over eight weeks also resulted in a significant improvement in NAS vs. baseline compared to vehicle-treated animals (FIGS. 2B, 2C): Whereas NAS increased by 0.8 points in the vehicle group, it decreased by 1.6 points in the group treated with the compound of SEQ ID NO.: 3 and by 0.3 points in the liraglutide group. Of note, the treatment effect of SEQ ID NO.: 3 was statistically significant versus both vehicle ($p<0.001$) and liraglutide ($p<0.05$). The mean fibrosis score increased upon vehicle treatment by 0.1 points, upon treatment with SEQ ID NO.: 4 by 0.2 points, whereas it remained unchanged in animals treated with compound SEQ ID NO.: 3. (FIG. 2D). Average baseline fibrosis scores were 1.5 for the vehicle group and the group treated with SEQ ID NO.: 3, and 1.4 for the liraglutide (SEQ ID NO.: 4) group, respectively.

Figure 3A:
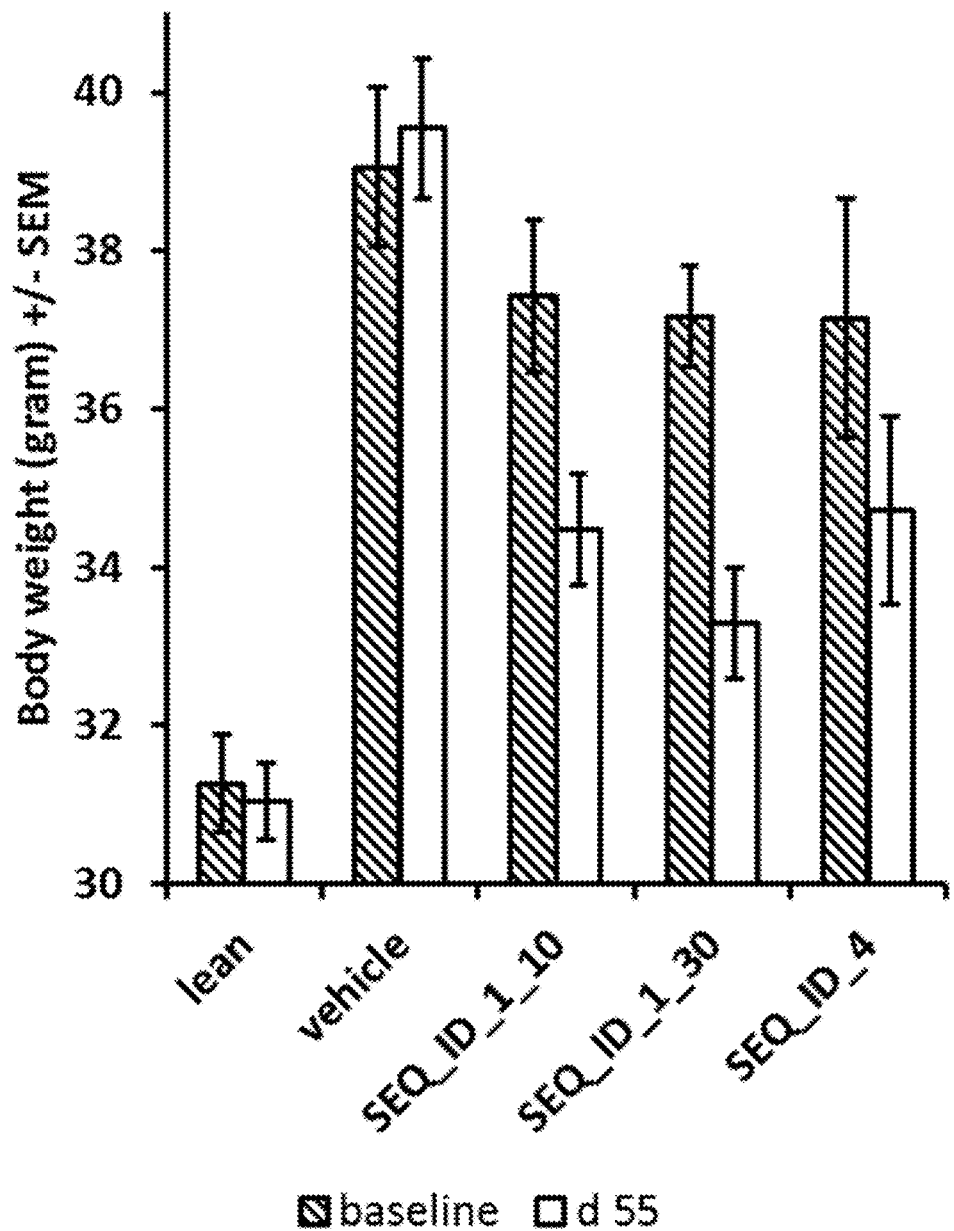
Figure 3B:
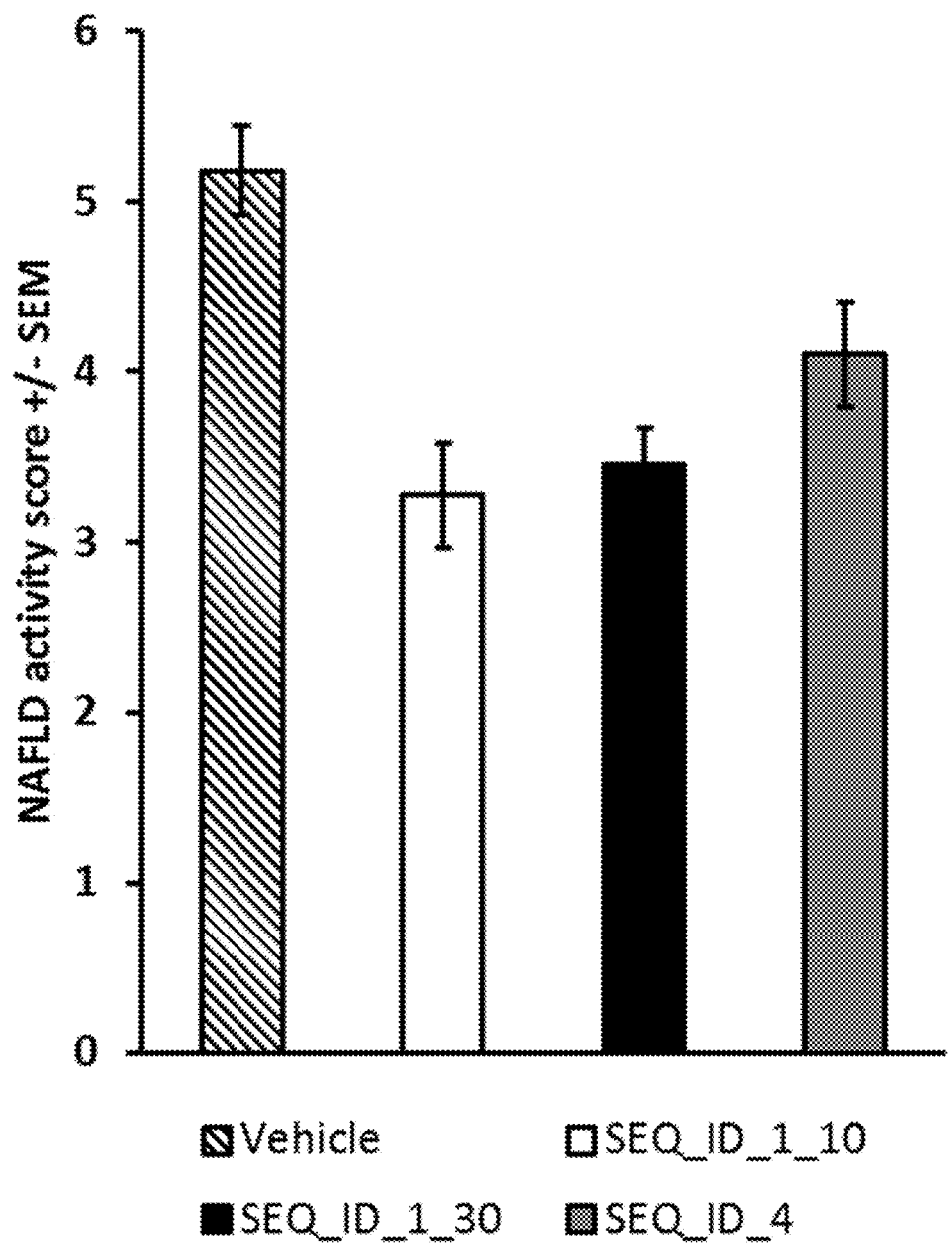
Figure 3C:
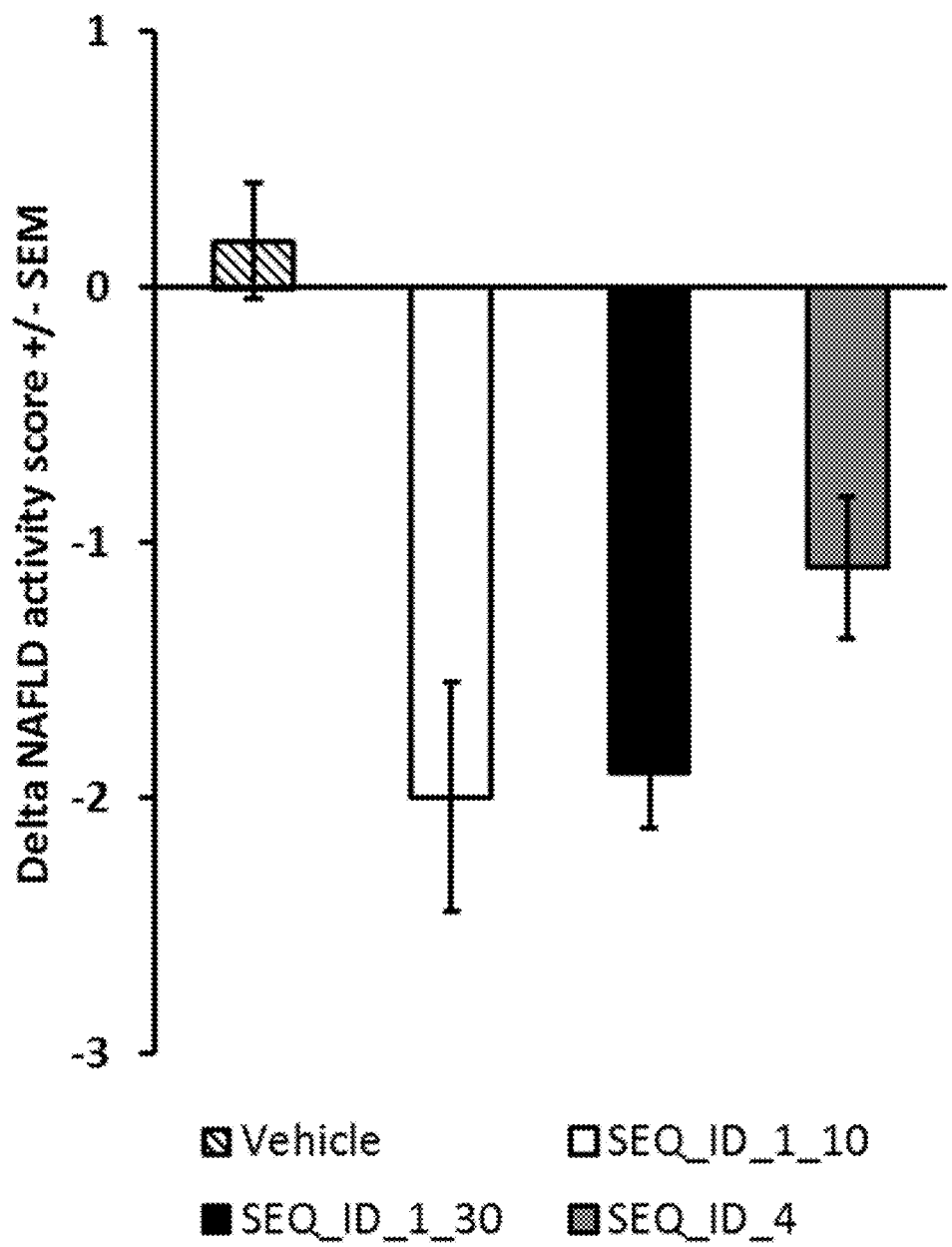
Figure 3D:
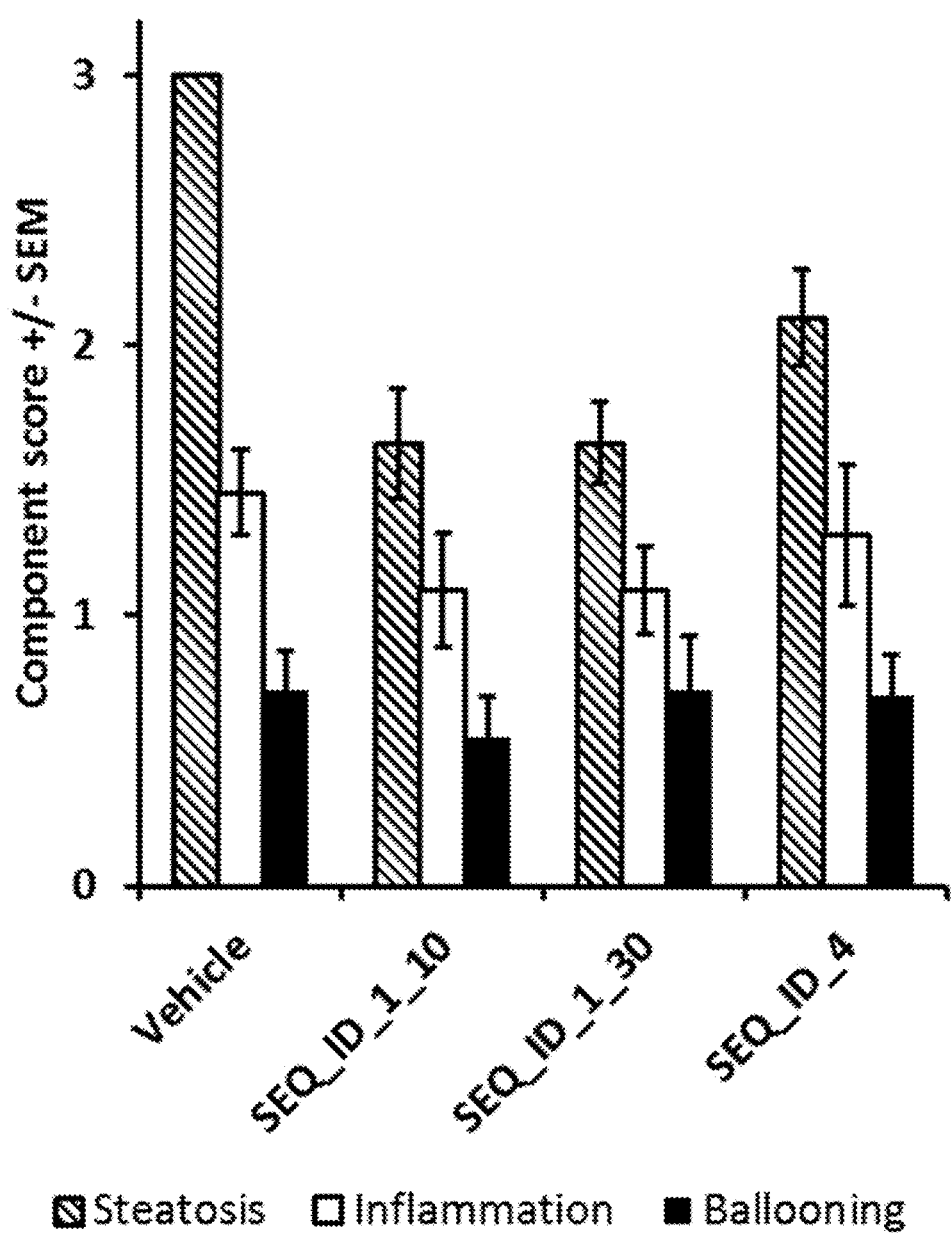
Figure 3E:
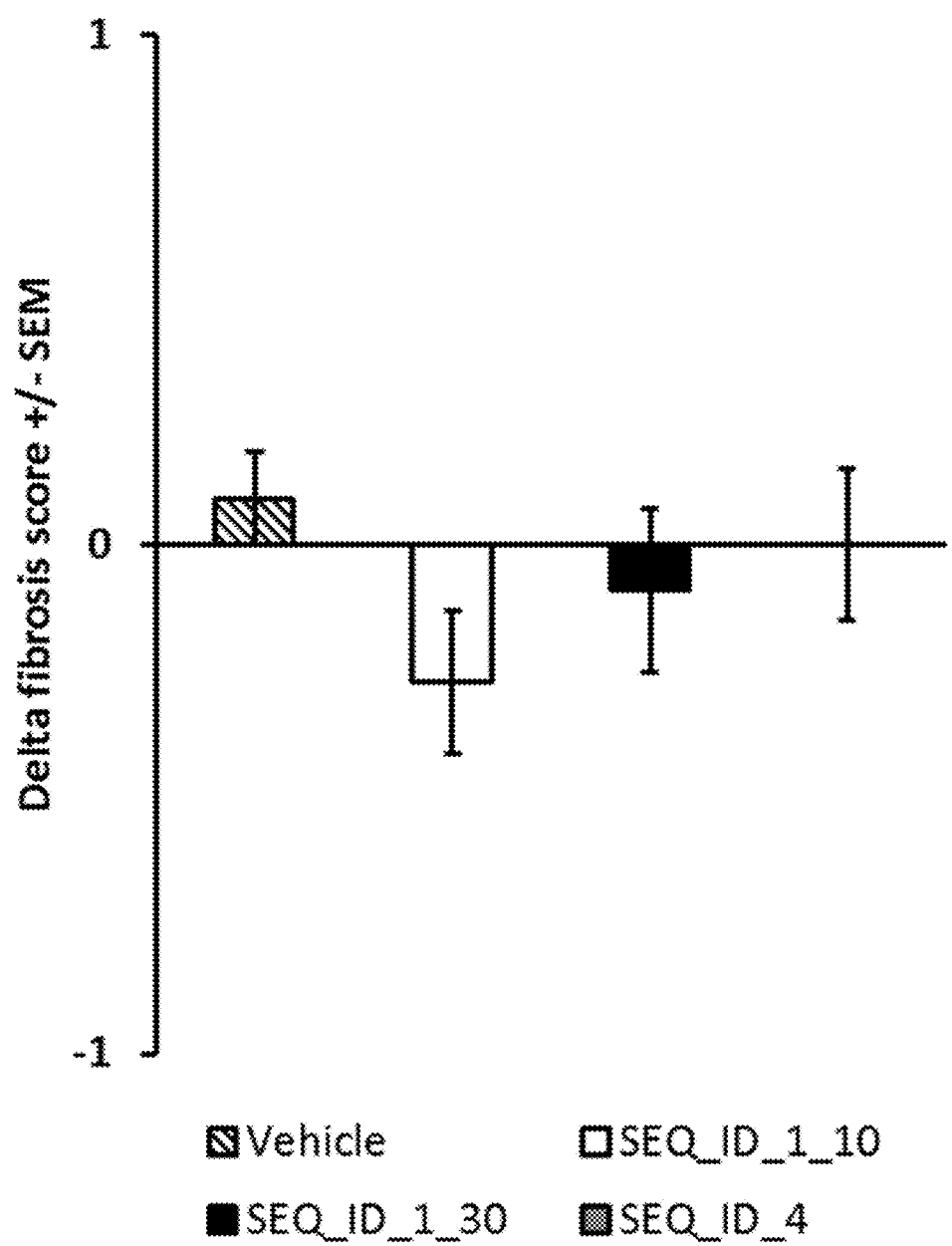

The compound of SEQ ID NO.: 1 at 10 or 30 μg/kg b.i.d. or liraglutide at 100 μg/kg b.i.d. led to a significant improvement in NAS vs baseline compared to vehicle: While the mean NAS increased by 0.2 points in the vehicle-treated animals, it decreased by 2.0 points with 10 μg/kg, by 1.9 points with 30 μg/kg SEQ ID NO.: 1 and by 1.1 points with liraglutide (FIGS. 3B, 3C). Improvement in NAS with the compound of SEQ ID NO.: 1 was significantly better than with liraglutide for the 30 μg/kg dose ($p<0.05$). A trend to an improvement in fibrosis was noted for both doses of the compound of SEQ ID NO.: 1 (FIG. 3E), but not for vehicle- or liraglutide (SEQ ID NO.: 4) treated animals. Baseline fibrosis levels were similar across the groups (1.3-1.6).

Thus, it was demonstrated that representative examples of the dual GLP1R/GCGR agonistic peptides of the present invention lead, at a similar degree of weight loss compared to the GLP1R agonist liraglutide, to pronounced improvement in NAFLD activity score.

Example 2: 48-Week Treatment of Biopsy-Proven Non-Alcoholic Steatohepatitis (NASH) with a Formulation Containing SEQ ID NO.: 1

Subject of the example is a double-blind, randomized, placebo-controlled, 48-weeks study to assess the effect of SEQ ID NO.: 1, a dual GLP-1/glucagon agonist, at daily subcutaneous doses of 200 μg in patients with and without type 2 diabetes mellitus with biopsy-proven non-alcoholic steatohepatitis (NASH) on disease progression.

Estimated patient enrolment is between approximately 60 and 120 randomized patients.

The primary study objective is to compare the effect of 200 μg SEQ ID NO.: 1 subcutaneous (SC) once daily versus placebo on histological resolution of non-alcoholic steatohepatitis (NASH) after 12 months of treatment vs baseline, defined as the ballooning component of the NAFLD activity score of zero in the absence of worsening of fibrosis.

The secondary study objectives are, inter alia, to assess from baseline to 12 months:
  Changes in the magnetic resonance imaging-based proton density fat fraction (MRI-PDFF) calculated total liver fat content (after 6 months of treatment vs baseline and after 12 months of treatment vs baseline)
  Changes in the overall NAFLD activity score at 12 months
  Changes in the individual components of the NAFLD activity score (steatosis, hepatocyte ballooning, lobular inflammation) at 12 months
  Changes in the Kleiner fibrosis stage at 12 months
  Pharmacokinetics of the compound of SEQ ID NO.:1

The study design is that of a randomized, placebo-controlled, double-blind, parallel-group study for SEQ ID NO.: 1 versus placebo.

SEQ ID NO.: 1 or placebo is provided as a solution for injection in cartridges containing 3 mL solution for injection, at a concentration of 500 μg/mL SEQ ID NO.: 1 or matching placebo. Tactipen® injector will be used to deliver subcutaneous doses of SEQ ID NO.: 1 and matching placebo. 3 dose steps (after starting dose) are planned for SEQ ID NO.: 1 during dose titration to reach a final targeted dose of 200 μg SC once daily (QD): 60-120-160-200 μg/day.

Doses should be administered in the morning at the same time and approximately 1 hour after breakfast for both SEQ ID NO.: 1 and placebo, except on clinic visit days. On the clinical visit days, SEQ ID NO.: 1 and placebo should be administered after blood test/ECG measurements in the morning and be coordinated with the PK sampling time.

SEQ ID NO.: 1 and matching placebo treatment regimens plan to include a 3-week dose increase period before the maintenance dose is reached, as follows:
  Active drug: 3 dose increase steps after 1 week each (if no significant tolerability issues [for example, nausea and vomiting] are observed):
    60 μg, ie, 12U/Day 1 to Day 7)
    120 μg, ie, 24U (Day 8 to Day 14)
    160 μg, ie, 32U (Day 15 to Day 21)
    200 μg, ie, 40U (from Day 22 on, this dose is intended to be administered for 49 weeks)
  Placebo: patients will be allocated to the same dose increase regimen.

At randomization, all patients randomized will start with the 60 μg daily dose step. The dose will be increased to 120 μg daily after one week treatment, if no significant tolerability issues (for example, nausea and vomiting) are observed. The dose will be further increased to 160 μg daily after one further week if no significant tolerability issues (for example, nausea and vomiting) are observed. The dose will finally be further increased to 200 μg daily after one further week if no significant tolerability issues (for example, nausea and vomiting) are observed.

The same dose increase regimen scheme will be conducted for patients assigned to placebo treatment, however with placebo instead of SEQ ID NO.: 1. The daily maintenance dose level will then be continued for the remainder of the treatment period (in total 49 weeks on final dose).

Primary endpoint of the study is the resolution of NASH, defined as hepatocyte ballooning score=0 and absence of lobular inflammation (score=0) or presence of mild lobular inflammation (score=1), without worsening in the Kleiner fibrosis score at 12 months and as compared to baseline.

Secondary endpoints of the study are, inter alia, changes in MRI-PDFF calculated total liver fat burden; changes in the overall NAFLD activity score; changes in the individual components of the NAFLD activity score (steatosis, hepatocyte ballooning, lobular inflammation); changes in the Kleiner fibrosis stage; and Pharmacokinetic parameters including apparent clearance (CL/F), volume of distribution (V/F), and $C_{trough}$ levels.

Patients will be assigned to either placebo or SEQ ID NO.: 1. There will be an approximately equal number of patients per each of the two treatment arms (placebo, SEQ ID NO.: 1).

The screening period will last for up to 6 weeks. Efficacy will be assessed at 12 months after randomization by a liver biopsy, for which patients could be hospitalized for up to 48 hours after the biopsy according to local guidelines and a 28 days posttreatment follow-up period.

Inclusion criteria for the study population are: Male and female patients, aged ≥18 and ≤75 years, with histologically confirmed presence of NASH (within the last 6 months prior to randomization) and FFPE-liver specimen available for re-analysis. Liver biopsy is allowed to be carried out during the screening phase. Histopathologic confirmation of NASH will be done by a central reading lab. NAFLD activity score has to be Patients have to be on diet/exercise and in case of diabetic patients on treatment with metformin (stable dose of ≥1500 mg/day or maximal tolerated dose) for at least 3 months prior to screening. Signed informed consent is required.

Main exclusion criteria are:
Any of the individual components of the NAFLD score (steatosis, ballooning, periportal inflammation) being <1
Kleiner fibrosis score of 4
Insulin dependent diabetes
HbA1c at screening visit >10.0%
FPG >270 mg/dL by the central laboratory at screening (Visit 1)
and confirmed by a repeat test prior to randomization
BMI <25 kg/m² or >45.0 kg/m²
Diagnosis of type 1 diabetes mellitus
Treatment with glucose-lowering agents(s) other than metformin,
currently or within the 3 months prior to screening
Previous insulin use, except for episode(s) of short-term treatment (≤15 consecutive days) for intercurrent illness, or use of insulin within the last 6 months
Contraindication(s) to use of GLP-1 analogues
Poorly controlled hypertension (a resting systolic blood pressure [SBP]>160 mm Hg and/or diastolic blood pressure [DBP]>95 mm Hg at screening)
History of long QT syndrome and/or QTc more than 450 ms at screening visit
History of pancreatitis or pancreatectomy
History of weight loss surgery
Personal or immediate family history of medullary thyroid cancer (MTC) or genetic conditions that predispose to MTC
Any prior exposure to drugs belonging to the class of GLP-1 receptor agonists or GLP-1 analogs
Contraindications or known hypersensitivity reaction to glucagon
Past medical history of liver transplantation, hepatocellular carcinoma (HCC), multiple endocrine neoplasia (MEN)
syndrome, malignancy (within last 3 years, exception of treated skin malignancy)
Other liver etiologies (i.e. drug-induced, viral hepatitis, autoimmune hepatitis, primary biliary cirrhosis, primary sclerosing cholangitis, hemochromatosis, alpha 1 anti-trypsin deficiency, Wilsons disease)
Participation in any clinical trial of an investigational therapy or agent within 3 months prior to randomization
NAS<4
Child's B or C cirrhosis
Liver enzymes >10-fold upper limit of normal
Average alcohol consumption per week >21 units (210 g) for males, >14 units (140 g) for females within the last 5 years
>5% weight loss since the diagnostic liver biopsy was obtained
Known positivity for antibody to human immunodeficiency virus (HIV)

The above information is not intended to contain all considerations relevant to a patient's potential participation in a clinical trial.

Example 3: 52-Week Treatment of Biopsy-Proven Non-Alcoholic Steatohepatitis (Nash) with a Formulation Containing SEQ ID NO.: 1

Subject of the example is a double-blind, randomized, placebo-controlled, 52-weeks study to assess the effect of two dose cohorts of SEQ ID NO.: 1, a dual GLP-1/glucagon agonist, at daily subcutaneous doses of up to either 120 µg or 200 µg in patients with and without type 2 diabetes mellitus with biopsy-proven non-alcoholic steatohepatitis (NASH) on disease progression in comparison to placebo.

Estimated patient enrolment is between approximately 90 and 150 randomized patients.

The primary study objective is to evaluate the dose response relationship of daily subcutaneous doses of two cohorts of up to 120 µg and up to 200 µg SEQ ID NO.: 1 compared to placebo and vs baseline on resolution of non-alcoholic steatohepatitis (NASH) with no worsening of fibrosis in diabetic and non-diabetic patients with histopathologically confirmed NASH.

The secondary study objectives are, inter alia, to assess from baseline to 12 months:
Changes in the magnetic resonance imaging-based proton density fat fraction (MRI-PDFF) calculated total liver fat content (after 6 months of treatment vs baseline and after 12 months of treatment vs baseline)
Changes in the overall NAFLD activity score at 12 months
Changes in the individual components of the NAFLD activity score (steatosis, hepatocyte ballooning, lobular inflammation) at 12 months
Changes in the Kleiner fibrosis stage at 12 months
Pharmacokinetics of the compound of SEQ ID NO.:1

The study design is that of a randomized, placebo-controlled, double-blind, parallel-group study for two dose levels of SEQ ID NO.: 1 versus placebo.

SEQ ID NO.: 1 or placebo is provided as a solution for injection in cartridges containing 3 mL solution for injection, at a concentration of 500 µg/mL SEQ ID NO.: 1 or matching placebo. Tactipen® injector will be used to deliver subcutaneous doses of SEQ ID NO.: 1 and matching placebo. An appropriate number of dose steps (after starting dose) is planned for SEQ ID NO.: 1 during dose titration to reach a final targeted dose of either 120 µg SC or 200 µg SC once daily (QD). The titration phase is intended to optimize the tolerability of the final dose, which should be reached within 14 weeks after the first dose.

Doses should be administered in the morning at the same time and approximately 1 hour after breakfast for both SEQ ID NO.: 1 and placebo, except on clinic visit days. On the clinical visit days, SEQ ID NO.: 1 and placebo should be administered after blood test/ECG measurements in the morning and be coordinated with the PK sampling time.

Both dose cohorts of SEQ ID NO.: 1 and matching placebo treatment regimens plan to include a dose increase period before the maintenance dose is reached after maximally 14 weeks, as follows:

Both cohorts of active drug: Appropriate number of weekly dose increase steps (if no significant tolerability issues [for example, nausea and vomiting] are observed):
20 μg, ie, 4U, Week 0, Day 1 to Day 7
40 μg, ie, 8U, reached earliest at Week 1, Day 8 to Day 14
60 μg, ie, 12U, reached earliest at Week 2, Day 15 to Day 21
Etc.
120 μg, ie 24U, reached earliest at Week 5, Day 36 to Day 42
140 μg, ie 28U, reached earliest at Week 6, Day 43 to Day 49
Etc.
200 μg, ie, 40U, reached earliest at Week 9, Day 64 to Day 70
Dose escalation can be suspended, doses can be reduced and doses can be increased again, depending on the tolerability of study medication.
Placebo: patients will be allocated to the same dose increase regimen.
After Week 14, Day 99, no further dose adjustments will be made.

At randomization, all patients randomized will start with the 20 μg daily dose step (or corresponding placebo). The dose will be increased in weekly steps of 20 μg as shown above until the targeted dose of 120 μg SC daily or 200 μg SC daily is reached and if no significant tolerability issues (for example, nausea and vomiting) are observed. The dose increase can be stopped, maintained at a tolerable level and can be increased again in weekly 20 μg SC dose steps if no significant tolerability issues (for example, nausea and vomiting) are observed, until the targeted dose levels are reached and tolerated. After Week 14, Day 99, no further dose adjustments will be allowed.

The same dose increase regimen scheme will be conducted for patients assigned to placebo treatment, however with placebo instead of SEQ ID NO.: 1.

After Week 14, Day 99 the maintenance dose level has to be reached and will not be changed for the remainder of the treatment period.

Primary endpoint of the study is the percentage of patients with resolution of NASH, defined as absence of hepatocyte ballooning (ballooning component of NAS=0) without worsening of fibrosis score at Week 52.

Secondary endpoints of the study are, inter alia,
Change from baseline to Week 26 and to Week 52 in MRI-PDFF-derived total liver fat, liver volume, and fractional liver fat content Percentage of patients who achieve status of no hepatocyte ballooning with lobular inflammation score of 0 or 1 without worsening of fibrosis score at Week 52
Percentage of patients who achieve an improvement of fibrosis by at least 1 stage without worsening of the hepatocyte ballooning component of NAS at Week 52
Change from baseline to Week 52 in the overall NAS
Change from baseline to Week 52 in individual components of NAS (steatosis, hepatocyte ballooning, and lobular inflammation) and in fibrosis score
Change from baseline in body weight, waist and hip circumference, and waist to hip ratio and
Pharmacokinetic parameters including apparent clearance (CL/F), volume of distribution (V/F), and $C_{trough}$ levels.

Patients will be assigned to either placebo or one of the two dose cohorts of SEQ ID NO.: 1. There will be an approximately equal number of patients per each of these three treatment arms (placebo, cohort 1 SEQ ID NO.: 1, cohort 2 SEQ ID NO.: 1).

The screening period will last for up to 8 weeks. Efficacy will be assessed at 12 months after randomization by a liver biopsy, for which patients could be hospitalized for up to 48 hours after the biopsy according to local guidelines.

There will be a 28 days posttreatment follow-up period.
Inclusion criteria for the study population are:
Male and female patients, aged ≥18 and ≤80 years, with histologically confirmed presence of NASH (within the last 6 months prior to randomization) and FFPE-liver specimen available for re-analysis. Liver biopsy is allowed to be carried out during the screening phase. Histopathologic confirmation of NASH will be done by a central reading laboratory. NAFLD activity score has to be Patients have to be on diet/exercise and in case of diabetic patients on treatment at a stable dose with metformin and/or sulfonylureas for at least 3 months prior to screening. Signed informed consent is required.

Main exclusion criteria are:
Any of the individual components of the NAFLD score (steatosis, ballooning, periportal inflammation) being <1
Kleiner fibrosis score of 4
Insulin dependent diabetes
HbA1c at screening visit ≥9.0%
FPG >270 mg/dL by the central laboratory at screening (Visit 1) and confirmed by a repeat test prior to randomization
BMI <25 kg/m$^2$ or >45.0 kg/m$^2$
Diagnosis of type 1 diabetes mellitus
Treatment (currently or within the 8 weeks prior to Randomization or 5 half-lives of the drug given, whichever is longer) with:
Glucose-lowering agent(s) other than metformin or sulfonylureas (eg, GLP-1-agonists, SGLT-2-inhibitors, glitazones, or DPP4-inhibitors)
Weight loss drugs, including orlistat
Systemic steroids
Methotrexate
Amiodarone
Vitamin E
Use of insulin within the last 6 months prior to Randomization, except for episode(s) of short-term treatment (<15 consecutive days) for intercurrent illness
Any prior exposure to drugs belonging to the class of GLP-1 receptor agonists or
GLP-1 analogs or contraindication(s) to use of GLP-1 agonists
Poorly controlled hypertension (a resting systolic blood pressure [SBP]>160 mm Hg and/or diastolic blood pressure [DBP]>95 mm Hg at screening)
History of cardiac conduction abnormalities including long QT syndrome
History of pancreatitis or pancreatectomy
History of weight loss surgery
Personal or immediate family history of medullary thyroid cancer (MTC) or genetic conditions that predispose to MTC Any prior exposure to drugs belonging to the class of GLP-1 receptor agonists or GLP-1 analogs Contraindications or known hypersensitivity reaction to glucagon Past medical history of liver transplantation, hepatocellular carcinoma (HCC), multiple endocrine neoplasia (MEN) syndrome, malignancy (within last 3 years, exception for treated skin malignancy)

Other liver etiologies (i.e. drug-induced, viral hepatitis, autoimmune hepatitis, primary biliary cirrhosis, primary sclerosing cholangitis, hemochromatosis, alpha 1 anti-trypsin deficiency, Wilsons disease)

Participation in any clinical trial of an investigational therapy or agent within 3 months prior to randomization

NAS<4

Liver enzymes >5-fold upper limit of normal

Average alcohol consumption per week >21 units (210 g) for males, >14 units (140 g) for females within the last 5 years Significant change (defined as 5% self-reported change) in body weight during the 2 months prior to screening for patients with liver biopsy collected during screening, or significant change (defined as 5% self-reported change in body weight) within 6 months prior to randomization if a pre-existing liver biopsy sample was collected prior to screening Period Known positivity for antibody to human immunodeficiency virus (HIV)

The above information is not intended to contain all considerations relevant to a patient's potential participation in a clinical trial.

The invention is further characterized by the following items.

Item 1. A compound or salt or solvate thereof having the general formula A His-(D-Ser)-Gln-Gly-Thr-Phe-Thr-Ser-Asp-Leu-Ser-Lys-Gln-X14-X15-X16-X17-X18-Ala-X20-Asp-Phe-Ile-Glu-Trp-Leu-Lys-X28-Gly-Gly-Pro-Ser-Ser-Gly-Ala-Pro-Pro-Pro-Ser-N H2
wherein
X14 is Lys, wherein the —NH$_2$ side chain group is functionalized by one of the groups selected from (S)-4-Carboxy-4-hexadecanoylamino-butyryl-(γE-Palm) and (S)-4-Carboxy-4-octadecanoylamino-butyryl-(γE-Stea);
X15 is Asp or Glu;
X16 is Ser or Glu;
X17 is Lys, Arg, or Gln;
X18 is Ala, Arg or Leu;
X20 is Gln or Lys; and
X28 is Ala or Asn;
for use in a method of preventing and/or treating metabolic liver disease.

Item 2. The compound or salt or solvate thereof of item 1 for use according to item 1, wherein
X14 is Lys, wherein the —NH$_2$ side chain group is functionalized by one of the groups selected from (S)-4-Carboxy-4-hexadecanoylamino-butyryl-(γE-Palm) and (S)-4-Carboxy-4-octadecanoylamino-butyryl-(γE-Stea);
X15 is Asp or Glu;
X16 is Ser or Glu;
X17 is Lys or Gln;
X18 is Ala or Leu;
X20 is Gln or Lys; and
X28 is Ala.

Item 3. The compound or salt or solvate thereof of item 1 for use according to item 1, wherein X14 is Lys, wherein the —NH$_2$ side chain group is functionalized by (S)-4-Carboxy-4-hexadecanoylamino-butyryl-(γE-Palm);
X15 is Asp or Glu;
X16 is Ser;
X17 is Lys or Arg;
X18 is Ala or Arg;
X20 is Gln; and
X28 is Ala or Asn.

Item 4. The compound or salt or solvate thereof of item 1 for use according to item 1, wherein the compound is SEQ ID NO.: 1 or a salt or solvate thereof.

Item 5. The compound or salt or solvate thereof of item 1 for use according to item 1, wherein the compound is SEQ ID NO.: 2 or a salt or solvate thereof.

Item 6. The compound or salt or solvate thereof of item 1 for use according to item 1, wherein the compound is SEQ ID NO.: 3 or a salt or solvate thereof.

Item 7. The compound or salt or solvate thereof of any one of items 1-6 for use according to any one of items 1-6, wherein said compound has a high solubility at an acidic pH, particularly between 3.5 and 5.5, more particularly about 4.5, and/or a physiological pH, particularly about 7.4, and wherein said solubility at said acidic and/or physiological pH is at least 0.5 mg/ml.

Item 8. A pharmaceutical composition comprising a compound or salt or solvate thereof of any one of items 1-7 as an active agent together with at least one pharmaceutically acceptable carrier, for use according to item 1.

Item 9. The pharmaceutical composition of item 8 for use according to item 1, wherein the pharmaceutical composition is parenterally administered, particularly injected.

Item 10. The pharmaceutical composition of item 8 or 9 for use according to item 1, wherein the pharmaceutical composition is administered in combination with at least one further therapeutically active ingredient.

Item 11. The compound or salt or solvate thereof of any one of items 1-7 or the pharmaceutical composition of any one of items 8-10 for use in a method of preventing and/or treating non-alcoholic fatty liver disease (NAFLD), particularly non-alcoholic fatty liver (NAFL), non-alcoholic steatohepatitis (NASH) and/or NAFLD-associated liver fibrosis.

Item 12. The compound or salt or solvate thereof of any one of items 1-7 or the pharmaceutical composition of any one of items 8-10 for use in a method of preventing non-alcoholic steatohepatitis (NASH), particularly NASH associated with fibrosis.

Item 13. The compound or salt or solvate thereof of any one of items 1-7 or the pharmaceutical composition of any one of items 8-10 for use in a method of treating non-alcoholic steatohepatitis (NASH), particularly NASH associated with fibrosis.

Item 14. A compound of SEQ ID NO.: 1 or a salt or solvate thereof or a pharmaceutical composition comprising a compound of SEQ ID NO.: 1 or a salt or solvate thereof as an active agent together with at least one pharmaceutically acceptable carrier, for use in a method of treating non-alcoholic steatohepatitis (NASH), particularly NASH associated with fibrosis.

Item 15. A compound of SEQ ID NO.: 2 or a salt or solvate thereof or a pharmaceutical composition comprising a compound of SEQ ID NO.: 2 or a salt or solvate thereof as an active agent together with at least one pharmaceutically acceptable carrier, for use in a method of treating non-alcoholic steatohepatitis (NASH), particularly NASH associated with fibrosis.

Item 16. A compound of SEQ ID NO.: 3 or a salt or solvate thereof or a pharmaceutical composition comprising a compound of SEQ ID NO.: 3 or a salt or solvate thereof as an active agent together with at least one pharmaceutically acceptable carrier, for use in a method of treating non-alcoholic steatohepatitis (NASH), particularly NASH associated with fibrosis.

Item 17. The compound or salt or solvate thereof of any one of items 1-7 or the pharmaceutical composition of any one of items 8-10 for use in a method of preventing and/or treating sequelae of non-alcoholic steatohepatitis (NASH), particularly NAFLD-related liver cirrhosis and/or NAFLD-related hepatocellular carcinoma.

Item 18. A compound of SEQ ID NO.: 1 or a salt or solvate thereof or a pharmaceutical composition comprising a compound of SEQ ID NO.: 1 or a salt or solvate thereof as an active agent together with at least one pharmaceutically acceptable carrier, for use in a method of preventing and/or treating sequelae of non-alcoholic steatohepatitis (NASH), particularly NAFLD-related liver cirrhosis and/or NAFLD-related hepatocellular carcinoma.

Item 19. A compound of SEQ ID NO.: 2 or a salt or solvate thereof or a pharmaceutical composition comprising a compound of SEQ ID NO.: 2 or a salt or solvate thereof as an active agent together with at least one pharmaceutically acceptable carrier, for use in a method of preventing and/or treating sequelae of non-alcoholic steatohepatitis (NASH), particularly NAFLD-related liver cirrhosis and/or NAFLD-related hepatocellular carcinoma.

Item 20. A compound of SEQ ID NO.: 3 or a salt or solvate thereof or a pharmaceutical composition comprising a compound of SEQ ID NO.: 3 or a salt or solvate thereof as an active agent together with at least one pharmaceutically acceptable carrier, for use in a method of preventing and/or treating sequelae of non-alcoholic steatohepatitis (NASH), particularly NAFLD-related liver cirrhosis and/or NAFLD-related hepatocellular carcinoma.

Item 21. The compound or salt or solvate thereof of any one of items 1-7 or the pharmaceutical composition of any one of items 8-10 for use in a method of simultaneously preventing and/or simultaneously treating NASH and additional pathological conditions or risk factors.

Item 22. The compound or salt or solvate thereof of any one of items 1-7 or the pharmaceutical composition of any one of items 8-10 for use in a method of simultaneously treating NASH and obesity.

Item 23. A compound of SEQ ID NO.: 1 or a salt or solvate thereof or a pharmaceutical composition comprising a compound of SEQ ID NO.: 1 or a salt or solvate thereof as an active agent together with at least one pharmaceutically acceptable carrier, for use in a method of simultaneously treating NASH and obesity.

Item 24. A compound of SEQ ID NO.: 2 or a salt or solvate thereof or a pharmaceutical composition comprising a compound of SEQ ID NO.: 2 or a salt or solvate thereof as an active agent together with at least one pharmaceutically acceptable carrier, for use in a method of simultaneously treating NASH and obesity.

Item 25. A compound of SEQ ID NO.: 3 or a salt or solvate thereof or a pharmaceutical composition comprising a compound of SEQ ID NO.: 3 or a salt or solvate thereof as an active agent together with at least one pharmaceutically acceptable carrier, for use in a method of simultaneously treating NASH and obesity.

Item 26. The compound or salt or solvate thereof of any one of items 1-7 or the pharmaceutical composition of any one of items 8-10 for use in a method of simultaneously treating NASH and type 2 diabetes mellitus.

Item 27. A compound of SEQ ID NO.: 1 or a salt or solvate thereof or a pharmaceutical composition comprising a compound of SEQ ID NO.: 1 or a salt or solvate thereof as an active agent together with at least one pharmaceutically acceptable carrier, for use in a method of simultaneously treating NASH and type 2 diabetes mellitus.

Item 28. A compound of SEQ ID NO.: 2 or a salt or solvate thereof or a pharmaceutical composition comprising a compound of SEQ ID NO.: 2 or a salt or solvate thereof as an active agent together with at least one pharmaceutically acceptable carrier, for use in a method of simultaneously treating NASH and type 2 diabetes mellitus.

Item 29. A compound of SEQ ID NO.: 3 or a salt or solvate thereof or a pharmaceutical composition comprising a compound of SEQ ID NO.: 3 or a salt or solvate thereof as an active agent together with at least one pharmaceutically acceptable carrier, for use in a method of simultaneously treating NASH and type 2 diabetes mellitus.

Item 30. The compound or salt or solvate thereof of any one of items 1-7 or the pharmaceutical composition of any one of items 8-10 for use in a method of simultaneously treating NASH and type 2 diabetes mellitus and obesity.

Item 31. A compound of SEQ ID NO.: 1 or a salt or solvate thereof or a pharmaceutical composition comprising a compound of SEQ ID NO.: 1 or a salt or solvate thereof as an active agent together with at least one pharmaceutically acceptable carrier, for use in a method of simultaneously treating NASH and type 2 diabetes mellitus and obesity.

Item 32. A compound of SEQ ID NO.: 2 or a salt or solvate thereof or a pharmaceutical composition comprising a compound of SEQ ID NO.: 2 or a salt or solvate thereof as an active agent together with at least one pharmaceutically acceptable carrier, for use in a method of simultaneously treating NASH and type 2 diabetes mellitus and obesity.

Item 33. A compound of SEQ ID NO.: 3 or a salt or solvate thereof or a pharmaceutical composition comprising a compound of SEQ ID NO.: 3 or a salt or solvate thereof as an active agent together with at least one pharmaceutically acceptable carrier, for use in a method of simultaneously treating NASH and type 2 diabetes mellitus and obesity.

Item 34. The compound or salt or solvate thereof of any one of items 1-7 or the pharmaceutical composition of any one of items 8-10 for use in a method of treating NASH, wherein a patient, particularly a human patient, is diagnosed as having NASH, if there is a presence of steatosis and hepatocyte ballooning and any degree of inflammation, or, alternatively, steatosis and advanced inflammation (score>1) in the absence of hepatocyte ballooning, with a Kleiner fibrosis score of <4.

Item 35. A compound of SEQ ID NO.: 1 or a salt or solvate thereof or a pharmaceutical composition comprising a compound of SEQ ID NO.: 1 or a salt or solvate thereof as an active agent together with at least one pharmaceutically acceptable carrier, for use in a method of treating NASH, wherein a patient, particularly a human patient, is diagnosed as having NASH, if there is a presence of steatosis and hepatocyte ballooning and any degree of inflammation, or, alternatively, steatosis and advanced inflammation (score>1) in the absence of hepatocyte ballooning, with a Kleiner fibrosis score of <4.

Item 36. A compound of SEQ ID NO.: 2 or a salt or solvate thereof or a pharmaceutical composition comprising a compound of SEQ ID NO.: 2 or a salt or solvate thereof as an active agent together with at least one pharmaceutically acceptable carrier, for use in a method of treating NASH, wherein a patient, particularly a human patient, is diagnosed as having NASH, if there is a presence of steatosis and hepatocyte ballooning and any degree of inflammation, or, alternatively, steatosis and advanced inflammation (score>1) in the absence of hepatocyte ballooning, with a Kleiner fibrosis score of <4.

Item 37. A compound of SEQ ID NO.: 3 or a salt or solvate thereof or a pharmaceutical composition comprising a compound of SEQ ID NO.: 3 or a salt or solvate thereof as an active agent together with at least one pharmaceutically acceptable carrier, for use in a method of treating NASH, wherein a patient, particularly a human patient, is diagnosed as having NASH, if there is a presence of steatosis and hepatocyte ballooning and any degree of inflammation, or, alternatively, steatosis and advanced inflammation (score>1) in the absence of hepatocyte ballooning, with a Kleiner fibrosis score of <4.

Item 38. The compound or salt or solvate thereof of any one of items 1-7 or the pharmaceutical composition of any one of items 8-10 for use in a method of treating NASH in a human patient, wherein the patient is considered as suffering from NASH, when, at the onset of treatment, (i) steatosis and hepatocyte ballooning scores are >0, or, in the absence of hepatocyte ballooning, steatosis score is >0 and inflammation score is >1, and (ii) a Kleiner fibrosis score of >0 and <4 is determined.

Item 39. A compound of SEQ ID NO.: 1 or a salt or solvate thereof or a pharmaceutical composition comprising a compound of SEQ ID NO.: 1 or a salt or solvate thereof as an active agent together with at least one pharmaceutically acceptable carrier, for use in a method of treating NASH in a human patient, wherein the patient is considered as suffering from NASH, when, at the onset of treatment, (i) steatosis and hepatocyte ballooning scores are each >0, or, in the absence of hepatocyte ballooning, steatosis score is >0 and inflammation score is >1, and (ii) a Kleiner fibrosis score of >0 and <4 is determined.

Item 40. A compound of SEQ ID NO.: 2 or a salt or solvate thereof or a pharmaceutical composition comprising a compound of SEQ ID NO.: 2 or a salt or solvate thereof as an active agent together with at least one pharmaceutically acceptable carrier, for use in a method of treating NASH in a human patient, wherein the patient is considered as suffering from NASH, when, at the onset of treatment, (i) steatosis and hepatocyte ballooning scores are each >0, or, in the absence of hepatocyte ballooning, steatosis score is >0 and inflammation score is >1, and (ii) a Kleiner fibrosis score of >0 and <4 is determined.

Item 41. A compound of SEQ ID NO.: 3 or a salt or solvate thereof or a pharmaceutical composition comprising a compound of SEQ ID NO.: 3 or a salt or solvate thereof as an active agent together with at least one pharmaceutically acceptable carrier, for use in a method of treating NASH in a human patient, wherein the patient is considered as suffering from NASH, when, at the onset of treatment, (i) steatosis and hepatocyte ballooning scores are each >0, or, in the absence of hepatocyte ballooning, steatosis score is >0 and inflammation score is >1, and (ii) a Kleiner fibrosis score of >0 and <4 is determined.

Item 42. The compound or salt or solvate thereof of any one of items 1-7 or the pharmaceutical composition of any one of items 8-10 for use in a method of treating NASH in a human patient suffering from NASH, but not suffering from type 2 diabetes mellitus and obesity, wherein the patient is considered as suffering from NASH, but not suffering from type 2 diabetes mellitus and obesity, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is <7 mmol/l and the plasma glucose concentration is <11.1 mmol/l in a glucose tolerance test two hours after an oral 75 g glucose load and the HbA1c value is <48 mmol/mol (<6.5%); and (iii) the BMI is <30.

Item 43. A compound of SEQ ID NO.: 1 or a salt or solvate thereof or a pharmaceutical composition comprising a compound of SEQ ID NO.: 1 or a salt or solvate thereof as an active agent together with at least one pharmaceutically acceptable carrier, for use in a method of treating NASH in a human patient suffering from NASH, but not suffering from type 2 diabetes mellitus and obesity, wherein the patient is considered as suffering from NASH, but not suffering from type 2 diabetes mellitus and obesity, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is <7 mmol/l and the plasma glucose concentration is <11.1 mmol/l in a glucose tolerance test two hours after an oral 75 g glucose load and the HbA1c value is <48 mmol/mol (<6.5%); and (iii) the BMI is <30.

Item 44. A compound of SEQ ID NO.: 2 or a salt or solvate thereof or a pharmaceutical composition comprising a compound of SEQ ID NO.: 2 or a salt or solvate thereof as an active agent together with at least one pharmaceutically acceptable carrier, for use in a method of treating NASH in a human patient suffering from NASH, but not suffering from type 2 diabetes mellitus and obesity, wherein the patient is considered as suffering from NASH, but not suffering from type 2 diabetes mellitus and obesity, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is <7 mmol/l and the plasma glucose concentration is <11.1 mmol/l in a glucose tolerance test two hours after an oral 75 g glucose load and the HbA1c value is <48 mmol/mol (<6.5%); and (iii) the BMI is <30.

Item 45. A compound of SEQ ID NO.: 3 or a salt or solvate thereof or a pharmaceutical composition comprising a compound of SEQ ID NO.: 3 or a salt or solvate thereof as an active agent together with at least one pharmaceutically acceptable carrier, for use in a method of treating NASH in a human patient suffering from NASH, but not suffering from type 2 diabetes mellitus and obesity, wherein the patient is considered as suffering from NASH, but not suffering from type 2 diabetes mellitus and obesity, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is <7 mmol/l and the plasma glucose concentration is <11.1 mmol/l in a glucose tolerance test two hours after an oral 75 g glucose load and the HbA1c value is <48 mmol/mol (<6.5%); and (iii) the BMI is <30.

Item 46. The compound or salt or solvate thereof of any one of items 1-7 or the pharmaceutical composition of any one of items 8-10 for use in a method of treating NASH and type 2 diabetes in a human patient suffering from NASH and type 2 diabetes mellitus, but not from obesity, wherein the patient is considered as suffering from NASH and type 2 diabetes mellitus, but not from obesity, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is ≥7 mmol/l, or/and the plasma glucose concentration is ≥11.1 mmol/l in a glucose tolerance test two hours after an oral 75 g glucose load, or/and the HbA1c value is ≥48 mmol/mol (≥6.5%); and (iii) the BMI is <30.

Item 47. A compound of SEQ ID NO.: 1 or a salt or solvate thereof or a pharmaceutical composition comprising a compound of SEQ ID NO.: 1 or a salt or solvate thereof as an active agent together with at least one pharmaceutically acceptable carrier, for use in a method of treating NASH and type 2 diabetes in a human patient suffering from NASH and type 2 diabetes mellitus, but not from obesity, wherein the patient is considered as suffering from NASH and type 2 diabetes mellitus, but not from obesity, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is ≥7 mmol/l, or/and the plasma glucose concentration is ≥11.1 mmol/l in a glucose tolerance test two hours after an oral 75 g glucose load, or/and the HbA1c value is ≥48 mmol/mol (≥6.5%); and (iii) the BMI is <30.

Item 48. A compound of SEQ ID NO.: 2 or a salt or solvate thereof or a pharmaceutical composition comprising a compound of SEQ ID NO.: 2 or a salt or solvate thereof as an active agent together with at least one pharmaceutically acceptable carrier, for use in a method of treating NASH and type 2 diabetes in a human patient suffering from NASH and type 2 diabetes mellitus, but not from obesity, wherein the patient is considered as suffering from NASH and type 2 diabetes mellitus, but not from obesity, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is ≥7 mmol/l, or/and the plasma glucose concentration is ≥11.1 mmol/l in a glucose tolerance test two hours after an oral 75 g glucose load, or/and the HbA1c value is ≥48 mmol/mol (≥6.5%); and (iii) the BMI is <30.

Item 49. A compound of SEQ ID NO.: 3 or a salt or solvate thereof or a pharmaceutical composition comprising a compound of SEQ ID NO.: 3 or a salt or solvate thereof as an active agent together with at least one pharmaceutically acceptable carrier, for use in a method of treating NASH and type 2 diabetes in a human patient suffering from NASH and type 2 diabetes mellitus, but not from obesity, wherein the patient is considered as suffering from NASH and type 2 diabetes mellitus, but not from obesity, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is ≥7 mmol/l, or/and the plasma glucose concentration is ≥11.1 mmol/l in a glucose tolerance test two hours after an oral 75 g glucose load, or/and the HbA1c value is ≥48 mmol/mol (≥6.5%); and (iii) the BMI is <30.

Item 50. The compound or salt or solvate thereof of any one of items 1-7 or the pharmaceutical composition of any one of items 8-10 for use in a method of treating NASH and obesity in a human patient suffering from NASH and obesity, but not from type 2 diabetes mellitus, wherein the patient is considered as suffering from NASH and obesity, but not from type 2 diabetes mellitus, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is <7 mmol/l and the plasma glucose concentration is <11.1 mmol/l in a glucose tolerance test two hours after an oral 75 g glucose load and the HbA1c value is <48 mmol/mol (<6.5%); and (iii) the BMI is ≥30.

Item 51. A compound of SEQ ID NO.: 1 or a salt or solvate thereof or a pharmaceutical composition comprising a compound of SEQ ID NO.: 1 or a salt or solvate thereof as an active agent together with at least one pharmaceutically acceptable carrier, for use in a method of treating NASH and obesity in a human patient suffering from NASH and obesity, but not from type 2 diabetes mellitus, wherein the patient is considered as suffering from NASH and obesity, but not from type 2 diabetes mellitus, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is <7 mmol/l and the plasma glucose concentration is <11.1 mmol/l in a glucose tolerance test two hours after an oral 75 g glucose load and the HbA1c value is <48 mmol/mol (<6.5%); and (iii) the BMI is ≥30.

Item 52. A compound of SEQ ID NO.: 2 or a salt or solvate thereof or a pharmaceutical composition comprising a compound of SEQ ID NO.: 2 or a salt or solvate thereof as an active agent together with at least one pharmaceutically acceptable carrier, for use in a method of treating NASH and obesity in a human patient suffering from NASH and obesity, but not from type 2 diabetes mellitus, wherein the patient is considered as suffering from NASH and obesity, but not from type 2 diabetes mellitus, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is <7 mmol/l and the plasma glucose concentration is <11.1 mmol/l in a glucose tolerance test two hours after an oral 75 g glucose load and the HbA1c value is <48 mmol/mol (<6.5%); and (iii) the BMI is ≥30.

Item 53. A compound of SEQ ID NO.: 3 or a salt or solvate thereof or a pharmaceutical composition comprising a compound of SEQ ID NO.: 3 or a salt or solvate thereof as an active agent together with at least one pharmaceutically acceptable carrier, for use in a method of treating NASH and obesity in a human patient suffering from NASH and obesity, but not from type 2 diabetes mellitus, wherein the patient is considered as suffering from NASH and obesity, but not from type 2 diabetes mellitus, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is <7 mmol/l and the plasma glucose concentration is <11.1 mmol/l in a glucose tolerance test two hours after an oral 75 g glucose load and the HbA1c value is <48 mmol/mol (<6.5%); and (iii) the BMI is ≥30.

Item 54. The compound or salt or solvate thereof of any one of items 1-7 or the pharmaceutical composition of any one of items 8-10 for use in a method of treating NASH and type 2 diabetes mellitus and obesity in a human patient suffering from NASH and type 2 diabetes mellitus and obesity, wherein the patient is considered as suffering from NASH and type 2 diabetes mellitus and obesity, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is ≥7 mmol/l, or/and the plasma glucose concentration is ≥11.1 mmol/l in a glucose tolerance test two hours after an oral 75 g glucose load, or/and the HbA1c value is ≥48 mmol/mol (≥6.5%); and (iii) the BMI is Item 55. A compound of SEQ ID NO.: 1 or a salt or solvate thereof or a pharmaceutical composition comprising a compound of SEQ ID NO.: 1 or a salt or solvate thereof as an active agent together with at least one pharmaceutically acceptable carrier, for use in a method of treating NASH and type 2 diabetes mellitus and obesity in a human patient suffering from NASH and type 2 diabetes mellitus and obesity, wherein the patient is considered as suffering from NASH and type 2 diabetes mellitus and obesity, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is ≥7 mmol/l, or/and the plasma glucose concentration is ≥11.1 mmol/l in a glucose tolerance test two hours after an oral 75 g glucose load, or/and the HbA1c value is ≥48 mmol/mol (≥6.5%); and (iii) the BMI is Item 56. A compound of SEQ ID NO.: 2 or a salt or solvate thereof or a pharmaceutical composition comprising a compound of SEQ ID NO.: 2 or a salt or solvate thereof as an active agent together with at least one pharmaceutically acceptable carrier, for use in a method of treating NASH and type 2 diabetes mellitus and obesity in a human patient suffering from NASH and type 2 diabetes mellitus and obesity, wherein the patient is considered as suffering from NASH and type 2 diabetes mellitus and obesity, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is ≥7 mmol/l, or/and the plasma glucose concentration is ≥11.1 mmol/l in a glucose tolerance test two hours after an oral 75 g glucose load, or/and the HbA1c value is ≥48 mmol/mol (≥6.5%); and (iii) the BMI is ≥30.

Item 57. A compound of SEQ ID NO.: 3 or a salt or solvate thereof or a pharmaceutical composition comprising a compound of SEQ ID NO.: 3 or a salt or solvate thereof as an active agent together with at least one pharmaceutically acceptable carrier, for use in a method of treating NASH and type 2 diabetes mellitus and obesity in a human patient suffering from NASH and type 2 diabetes mellitus and obesity, wherein the patient is considered as suffering from NASH and type 2 diabetes mellitus and obesity, when, at the onset of treatment, (i) (a) the steatosis and hepatocyte ballooning scores are each >0 and the inflammation score is 0-3, or (b) the steatosis score is >0 and the inflammation score is >1 in the absence of hepatocyte ballooning, wherein according to both (a) and (b) the Kleiner fibrosis score is <4;

(ii) the fasting plasma glucose concentration is ≥7 mmol/l, or/and the plasma glucose concentration is ≥11.1 mmol/l in a glucose tolerance test two hours after an oral 75 g glucose load, or/and the HbA1c value is ≥48 mmol/mol (≥6.5%); and (iii) the BMI is ≥30.

Item 58. A method of preventing or treating metabolic liver disease in a patient in need thereof, comprising administering to said patient a therapeutically effective amount of a compound or salt or solvate thereof having the general formula A

```
His-(D-Ser)-Gln-Gly-Thr-Phe-Thr-Ser-Asp-Leu-Ser-

Lys-Gln-X14-X15-X16-X17-X18-Ala-X20-Asp-Phe-Ile-

Glu-Trp-Leu-Lys-X28-Gly-Gly-Pro-Ser-Ser-Gly-Ala-

Pro-Pro-Pro-Ser-NH2
``` wherein

X14 is Lys, wherein the —NH2 side chain group is functionalized by one of the groups selected from (S)-4-Carboxy-4-hexadecanoylamino-butyryl-(γE-Palm) and (S)-4-Carboxy-4-octadecanoylamino-butyryl-(γE-Stea);

X15 is Asp or Glu;

X16 is Ser or Glu;

X17 is Lys, Arg, or Gln;

X18 is Ala, Arg or Leu;

X20 is Gln or Lys; and

X28 is Ala or Asn.

The invention claimed is:

1. A method for treating non-alcoholic fatty liver disease (NAFLD) comprising administering to a subject in need thereof a compound or salt or solvate thereof having the general formula A:

His-(D-Ser)-Gln-Gly-Thr-Phe-Thr-Ser-Asp-Leu-Ser-Lys-Gln-X14-X15-X16-X17-X18-Ala-X20-Asp-Phe-Ile-Glu-Trp-Leu-Lys-X28-Gly-Gly-Pro-Ser-Ser-Gly-Ala-Pro-Pro-Pro-Ser-NH2 wherein:
the non-alcoholic fatty liver disease is non-alcoholic steatohepatitis (NASH);
the subject is between 18 and 75 years of age and has a body mass index between 25 and 45 kg/m$^2$;
X14 is Lys, wherein the —NH2 side chain group is functionalized by one of the groups selected from (S)-4-Carboxy-4-hexadecanoylamino-butyryl-(γE-Palm) and (S)-4-Carboxy-4-octadecanoylamino-butyryl-(γE-Stea);
X15 is Asp or Glu;
X16 is Ser or Glu;
X17 is Lys, Arg, or Gln;
X18 is Ala, Arg or Leu;
X20 is Gln or Lys; and
X28 is Ala or Asn.

2. The method of claim 1, wherein the non-alcoholic steatohepatitis is associated with fibrosis.

3. The method of claim 1, wherein the method treats additional pathological conditions or risk factors, and wherein the additional pathological conditions or risk factors are obesity and/or type 2 diabetes mellitus.

4. The method of claim 1, wherein:
X14 is Lys, wherein the —NH2 side chain group is functionalized by one of the groups selected from (S)-4-Carboxy-4-hexadecanoylamino-butyryl-(γE-Palm) and (S)-4-Carboxy-4-octadecanoylamino-butyryl-(γE-Stea);
X15 is Asp or Glu;
X16 is Ser or Glu;
X17 is Lys or Gln;
X18 is Ala or Leu;
X20 is Gln or Lys; and
X28 is Ala.

5. The method of claim 1, wherein:
X14 is Lys, wherein the —NH2 side chain group is functionalized by (S)-4-Carboxy-4-hexadecanoylamino-butyryl-(γE-Palm);
X15 is Asp or Glu;
X16 is Ser;
X17 is Lys or Arg;
X18 is Ala or Arg;
X20 is Gln; and
X28 is Ala or Asn.

6. The method of claim 1, wherein the compound is any one of SEQ ID NO: 1, SEQ ID NO: 2, SEQ ID NO: 3, or a salt or solvate thereof.

7. The method of claim 1, wherein said compound has a high solubility at an acidic pH and/or a physiological pH.

8. The method of claim 7, wherein the pH is between 3.5 and 5.5.

9. The method of claim 8, wherein the pH is about 4.5.

10. The method of claim 7, wherein the pH is about 7.4.

11. A method for treating non-alcoholic fatty liver disease (NAFLD) comprising administering to a patient in need thereof a pharmaceutical composition comprising a compound or salt or solvate thereof of formula A as an active agent together with at least one pharmaceutically acceptable carrier, wherein the general formula A is: His-(D-Ser)-Gln-Gly-Thr-Phe-Thr-Ser-Asp-Leu-Ser-Lys-Gln-X14-X15-X16-X17-X18-Ala-X20-Asp-Phe-Ile-Glu-Trp-Leu-Lys-X28-Gly-Gly-Pro-Ser-Ser-Gly-Ala-Pro-Pro-Pro-Ser-NH2 wherein:
the non-alcoholic fatty liver disease is non-alcoholic steatohepatitis (NASH);
the subject is between 18 and 75 years of age and has a body mass index (BMI) between 25 and 45 kg/m²;
X14 is Lys, wherein the —NH2 side chain group is functionalized by one of the groups selected from (S)-4-Carboxy-4-hexadecanoylamino-butyryl-(γE-Palm) and (S)-4-Carboxy-4-octadecanoylamino-butyryl-(γE-Stea);
X15 is Asp or Glu;
X16 is Ser or Glu;
X17 is Lys, Arg, or Gln;
X18 is Ala, Arg or Leu;
X20 is Gln or Lys; and
X28 is Ala or Asn.

12. The method of claim 11, wherein the pharmaceutical composition is parenterally administered.

13. The method of claim 12, wherein the pharmaceutical composition is injected.

14. The method of claim 11, wherein the pharmaceutical composition is administered in combination with at least one further therapeutically active ingredient.

15. The method of claim 1, wherein the subject has at the onset of the treatment:
(i) hepatocyte ballooning and steatosis scores greater than 0, or a hepatocyte ballooning score of 0, a steatosis score greater than 0, and an inflammation score greater than 1; and
(ii) a Kleiner fibrosis score between 0 and 4.

16. The method of claim 1, wherein the subject achieves after treatment:
(i) a decrease in the NAFLD activity score (NAS) and no increase in the Kleiner fibrosis score; or
(ii) no increase in the NAFLD activity score (NAS) and a decrease in the Kleiner fibrosis score.

17. A method for treating non-alcoholic fatty liver disease (NAFLD) comprising administering to a subject in need thereof a compound or salt or solvate thereof having the general formula A:

His-(D-Ser)-Gln-Gly-Thr-Phe-Thr-Ser-Asp-Leu-Ser-Lys-Gln-X14-X15-X16-X17-X18-Ala-X20-Asp-Phe-Ile-Glu-Trp-Leu-Lys-X28-Gly-Gly-Pro-Ser-Ser-Gly-Ala-Pro-Pro-Pro-Ser-NH₂ wherein:
the non-alcoholic fatty liver disease is non-alcoholic steatohepatitis (NASH);
the subject is between 18 and 75 years of age and has a body mass index between 25 and 45 kg/m²;
the subject has at the onset of the treatment:
(i) hepatocyte ballooning and steatosis scores greater than 0, or a hepatocyte ballooning score of 0, a steatosis score greater than 0, and an inflammation score greater than 1; and
(ii) a Kleiner fibrosis score between 0 and 4;
the subject achieves after treatment no increase in the NAFLD activity score (NAS) and a decrease in the Kleiner fibrosis score;
X14 is Lys, wherein the —NH2 side chain group is functionalized by one of the groups selected from (S)-4-Carboxy-4-hexadecanoylamino-butyryl-(γE-Palm) and (S)-4-Carboxy-4-octadecanoylamino-butyryl-(γE-Stea);
X15 is Asp or Glu;
X16 is Ser or Glu;
X17 is Lys, Arg, or Gln;
X18 is Ala, Arg or Leu;
X20 is Gln or Lys; and
X28 is Ala or Asn.

* * * * *

SEQUENCE LISTING

<160> NUMBER OF SEQ ID NOS: 4

<210> SEQ ID NO 1
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: amidated C-terminus

<400> SEQUENCE: 1

His Xaa Gln Gly Thr Phe Thr Ser Asp Leu Ser Lys Gln Lys Glu Ser
1               5                   10                  15

Lys Ala Ala Gln Asp Phe Ile Glu Trp Leu Lys Ala Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (14)..(14)
<223> OTHER INFORMATION: Lys is functionalized at the amino side chain
      group as Lys((S)-4-carboxy-4-hexadecanoylamino-butyryl)
<220> FEATURE:
<221> NAME/KEY: MOD_RES
<222> LOCATION: (39)..(39)
<223> OTHER INFORMATION: amidated C-terminus

<400> SEQUENCE: 2

His Xaa Gln Gly Thr Phe Thr Ser Asp Leu Ser Lys Gln Lys Asp Ser
1               5                   10                  15

Arg Arg Ala Gln Asp Phe Ile Glu Trp Leu Lys Asn Gly Gly Pro Ser
            20                  25                  30

Ser Gly Ala Pro Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: Exendin-4 analogue
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES

```
<222> LOCATION: (14)..(14)
<223> OTHER INFORMATION: Lys is functionalized at the amino side chain
      group as Lys((S)-4-carboxy-4-octadecanoylamino-butyryl)
<220> FEATURE:
<221> NAME/KEY: MOD_RES
<222> LOCATION: (39)..(39)
<223> OTHER INFORMATION: amidated C-terminus

<400> SEQUENCE: 3

His Xaa Gln Gly Thr Phe Thr Ser Asp Leu Ser Lys Gln Lys Asp Glu
1               5                   10                  15

Gln Leu Ala Lys Asp Phe Ile Glu Trp Leu Lys Ala Gly Gly Pro Ser
            20                  25                  30

Ser Gly Ala Pro Pro Pro Ser
        35

<210> SEQ ID NO 4
<211> LENGTH: 31
<212> TYPE: PRT
<213> ORGANISM: Artificial Sequence
<220> FEATURE:
<223> OTHER INFORMATION: Liraglutide
<220> FEATURE:
<221> NAME/KEY: MOD_RES
<222> LOCATION: (20)..(20)
<223> OTHER INFORMATION: Lys is functionalized at the amino side chain
      group as Lys((S)-4-carboxy-4-hexadecanoylamino-butyryl)

<400> SEQUENCE: 4

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30
```